US011940381B2

(12) United States Patent
Wu et al.

(10) Patent No.: US 11,940,381 B2
(45) Date of Patent: Mar. 26, 2024

(54) CALIBRATION OF MULTISPECTRAL ANALYSIS SYSTEMS

(71) Applicant: Revvity Health Sciences, Inc., Waltham, MA (US)

(72) Inventors: Rongcong Wu, Auburndale, MA (US); Daniel Schoener, Newton, MA (US)

(73) Assignee: Revvity Health Sciences, Inc., Waltham, MA (US)

( * ) Notice: Subject to any disclaimer, the term of this patent is extended or adjusted under 35 U.S.C. 154(b) by 548 days.

(21) Appl. No.: 16/435,898

(22) Filed: Jun. 10, 2019

(65) Prior Publication Data
US 2020/0011793 A1  Jan. 9, 2020

Related U.S. Application Data

(60) Provisional application No. 62/682,819, filed on Jun. 8, 2018.

(51) Int. Cl.
*G01N 21/64* (2006.01)
*C12Q 1/6851* (2018.01)
*G01N 21/27* (2006.01)

(52) U.S. Cl.
CPC ......... *G01N 21/645* (2013.01); *C12Q 1/6851* (2013.01); *G01N 21/278* (2013.01); *G01N 21/6428* (2013.01)

(58) Field of Classification Search
CPC ............... G01N 21/645; G01N 21/278; G01N 21/6428; G01N 33/533; C12Q 1/6851
See application file for complete search history.

(56) References Cited

U.S. PATENT DOCUMENTS

| 4,868,126 | A | 9/1989 | Schwartz |
| 5,073,497 | A | 12/1991 | Schwartz |
| 6,982,431 | B2 * | 1/2006 | Modlin ............... G01N 21/6452 250/225 |
| 2003/0128371 | A1 * | 7/2003 | Vaux ...................... G01N 13/02 356/601 |
| 2005/0255485 | A1 * | 11/2005 | Livak ..................... G16B 20/20 435/6.17 |
| 2008/0001099 | A1 | 1/2008 | Sharaf et al. |

(Continued)

FOREIGN PATENT DOCUMENTS

| CN | 102410879 | 4/2012 |
| CN | 104244826 | 12/2014 |

OTHER PUBLICATIONS

International Search Report and Written Opinion in corresponding Application No. PCT/US2019/036290, dated Aug. 30, 2019, pp. 1-24.

(Continued)

*Primary Examiner* — Samuel P Siefke
*Assistant Examiner* — Henry H Nguyen
(74) *Attorney, Agent, or Firm* — Fish & Richardson P.C.

(57) ABSTRACT

Methods for calibrating a multispectral analysis system include calibrating the system to detect fluorescence emission from a first fluorescent entity in a biological sample that includes the first fluorescent entity and a second fluorescent entity using a calibration sample, where the calibration sample features a first concentration of the first fluorescent entity and a second concentration of the second fluorescent entity, and where the first concentration is larger than the second concentration.

24 Claims, 10 Drawing Sheets

(56) References Cited

U.S. PATENT DOCUMENTS

| | | | |
|---|---|---|---|
| 2008/0018898 A1* | 1/2008 | Gunstream | G01N 21/274 356/416 |
| 2008/0178653 A1 | 7/2008 | Gunstream | |
| 2011/0301062 A1 | 12/2011 | Zhu et al. | |
| 2015/0160132 A1* | 6/2015 | Hulme | G01N 21/274 436/8 |
| 2016/0228876 A1* | 8/2016 | Chu | G01N 21/6486 |
| 2016/0231246 A1 | 8/2016 | Chu et al. | |
| 2016/0237474 A1* | 8/2016 | Marks | G01N 21/274 |
| 2017/0152550 A1* | 6/2017 | Hiddessen | G01N 21/6428 |

OTHER PUBLICATIONS

Schwartz et al., "Standardizing Flow Cytometry: A Classification System of Fluorescence Standards Used for Flow Cytometry," vol. 33(2):106-114, Oct. 1, 1998.

Kumar Keshav et al., "Understanding the effect of calibration set design for the application of MCR-ALS analysis on excitation-emission matrix fluorescence (EEMF) data sets under commonly used non-negativity constraints," Chemometrics and Intelligent Laboratory Systems, Elsevier Science Publishers B.V., vol. 149:70-77, Oct. 22, 2015.

* cited by examiner

CALIBRATION OF MULTISPECTRAL ANALYSIS SYSTEMS

CROSS-REFERENCE TO RELATED APPLICATIONS

This application claims priority to U.S. Provisional Patent Application No. 62/682,819, filed on Jun. 8, 2018, the entire contents of which are incorporated by reference herein.

BACKGROUND

Multispectral analysis systems can be used in a variety of assays to determine information about fluorophore and chromophore binding and expression in biological samples. Typically, where multiple spectral contributors in a sample emit or absorb radiation, contributions from each of the spectral contributors are separated to individually assess attributes such as the spatial location and concentration of each contributor. Such assessments can provide important information about a sample, including disease status, immunological response, protein expression, and the efficacy of pharmaceutical treatment.

Multispectral analysis systems are typically calibrated prior to undertaking assessment of samples. Calibration generally involves undertaking various steps to ensure that such systems can resolve individual contributions from different spectral contributors.

SUMMARY

The methods and devices disclosed herein use mixtures of calibration dyes in single calibration plate wells to calibrate multispectral imaging systems. In particular, mixtures of calibration dyes are used to reduce or eliminate cross-talk among spectral channels that are relatively closely spaced. Cross-talk impairs recovery of accurate quantitative information from a variety of assays by allowing contributions from one spectral contributor to contaminate or obscure contributions from another spectral contributor.

In methods and devices disclosed herein, by calibrating with mixtures of calibration dyes, the "background" contributions of an interfering spectral contributor to measured emission or absorption from a spectral contributor of interest can be reduced or eliminated. As a result, spectral cross-talk is reduced and spectral multiplexing is enhanced. In other words, by using mixtures of calibration dyes at particular calibration wavelengths or bands, the number of different fluorophores in a sample that can be analyzed can be increased, and contributions from fluorophores with emission spectra that at least partially overlap can be distinguished and quantitatively analyzed with accuracy and precision.

In general, in a first aspect, the disclosure features methods for calibrating a multispectral analysis system that include calibrating the system to detect fluorescence emission from a first fluorescent entity in a biological sample that includes the first fluorescent entity and a second fluorescent entity using a calibration sample, where the calibration sample features a first concentration of the first fluorescent entity and a second concentration of the second fluorescent entity, and where the first concentration is larger than the second concentration.

Embodiments of the methods can include any one or more of the following features.

The first fluorescent entity can be Cy5 and the second fluorescent entity can be Cy5.5. The calibration sample can be a calibration plate that includes a plurality of sample wells.

A fluorescence emission spectrum of the first fluorescent entity can least partially overlap with a fluorescence emission spectrum of the second fluorescent entity. The first and second fluorescent entities can each be associated with spectral emission channels in the multispectral analysis system, and fluorescence emission from the first fluorescent entity can be detected by the multispectral analysis system in the spectral emission channel associated with the second fluorescent entity.

The first and second fluorescent entities can each be fluorescent dyes. The first fluorescent entity can be an endogenous fluorescent moiety, and the second fluorescent entity can be a fluorescent dye. A fraction of the second fluorescent entity in the calibration sample relative to a total amount of the first and second fluorescent entities in the calibration sample can be between 0.02 and 0.08 (e.g., between 0.03 and 0.07, between 0.04 and 0.06).

The methods can include using the calibrated multispectral analysis system to identify one or more gene targets in the biological sample.

Embodiments of the methods can also include any of the other features disclosed herein, including any combinations of individual features disclosed in connection with different embodiments, except as expressly stated otherwise.

In another aspect, the disclosure features calibration samples that include a calibration plate featuring a plurality of sample wells, where the calibration plate is dimensioned to be received in a multispectral analysis system, and a calibration composition positioned in one or more of the wells, the composition including a first fluorescent entity and a second fluorescent entity, where a fluorescence emission spectrum of the first fluorescent entity overlaps at least partially with a fluorescence emission spectrum of the second fluorescent entity.

Embodiments of the calibration samples can include any one or more of the following features.

A fraction of the second fluorescent entity in the composition relative to a total amount of the first and second fluorescent entities in the composition can be between 0.02 and 0.08 (e.g., between 0.03 and 0.07, between 0.04 and 0.06). The first fluorescent entity can be Cy5 and the second fluorescent entity can be Cy5.5.

Embodiments of the calibration samples can also include any of the other features disclosed herein, including any combinations of individual features disclosed in connection with different embodiments, except as expressly stated otherwise.

In a further aspect, the disclosure features methods that include calibrating a multispectral analysis system to detect fluorescence emission from multiple fluorescent dyes in a biological sample, where fluorescence emission is detected in a different spectral channel of the system for each of the different fluorescent dyes, and where, for a first fluorescent dye in the biological sample, the calibrating includes introducing into the system a calibration sample corresponding to the first fluorescent dye and featuring a first amount of the first fluorescent dye and a second amount of a second fluorescent dye in the biological sample.

Embodiments of the methods can include any one or more of the following features.

The first and second fluorescent dyes can have respective first and second fluorescence emission spectra that at least partially overlap. Fluorescence emission from the first fluorescent dye can be detected in a first spectral channel of the detection system and fluorescence emission from the second fluorescent dye can be detected in a second spectral channel of the detection system, and at least a portion of fluorescence emission from the first fluorescent dye can also be detected in the second spectral channel. The first fluorescent dye can be Cy5 and the second fluorescent dye can be Cy5.5.

Embodiments of the methods can also include any of the other features disclosed herein, including any combinations of individual features disclosed in connection with different embodiments, except as expressly stated otherwise.

The details of one or more embodiments are set forth in the accompanying drawings and the description below. Other features and advantages will be apparent from the description, drawings, and claims.

DESCRIPTION OF DRAWINGS

Like reference symbols in the drawings indicate like elements.

DETAILED DESCRIPTION

Multispectral analysis systems typically include different filters for use in quantitatively measuring contributions from specific fluorophores in a biological sample. When a sample is prepared with (or expresses) multiple fluorophores, each of which has a different emission spectrum, emission from each of the fluorophores can be isolated for analysis by selecting a corresponding filter with a central wavelength and bandpass filter that effectively excludes emission from all fluorophores in the sample but the fluorophore of interest. As the number of fluorophores increases, and for fluorophores with relatively wide spectral emission bandwidths, it is increasingly challenging to implement spectral filters that isolate emission from each fluorophore by sufficiently excluding emission from the others, and at the same time transmit sufficient emission radiation from the fluorophore of interest to generate a detectable signal.

As an example, the QuantStudio™ Dx imaging system (available from ThermoFisher Scientific, Waltham, MA) uses a filter designated m5 to quantify spectral emission from Cy5 dye in samples (excited at a wavelength of 648 nm, and fluoresces at a nominal wavelength of 668 nm), and a filter designated m6 to quantify spectral emission from Cy5.5 dye in samples (excited at 685 nm, and fluoresces at a nominal wavelength of 706 nm). Both Cy5 and Cy5.5 dyes have significant fluorescence emission bandwidth and spectral overlap. Note that in this disclosure, "Cyanine" is abbreviated as "Cy".

Various assays and other quantitative analysis techniques rely on accurate quantification of multiple fluorophores in a single sample for imaging and diagnostic purposes. One such assay is the NeoMDx® qPCR assay (available from Perkin Elmer, Waltham, MA), which is a multiplex polymerase chain reaction (PCR) assay that uses dyes ROX™, FAM™, HEX™ Cy5, and Cy5.5 in a single PCR reaction.

A multispectral analysis system (such as the QuantStudio™ Dx) is used in this assay to measure, separate, and quantify fluorescence emission from each of these dyes during PCR reaction cycling. These dyes are used to target the following genes in samples:

TABLE 1

| Dye | Sample Target Gene |
|---|---|
| ROX | None (reference dye) |
| FAM | TREC |
| HEX | RPP30 |
| Cy5 | SMN1 |
| Cy5.5 | KREC |

As shown in Table 1, during sample preparation prior to performing the assay, the SMN1 target gene is labeled with the Cy5 fluorophore, and the KREC target gene is labeled with the Cy5.5 fluorophore. Using the dyes listed in Table 1, the NeoMDx™ qPCR multiplex assay can detect the presence or absence of gene targets TREC, SMN1, and KREC in a sample, along with the presence or absence of the RPP30 reference gene.

Figure 1:
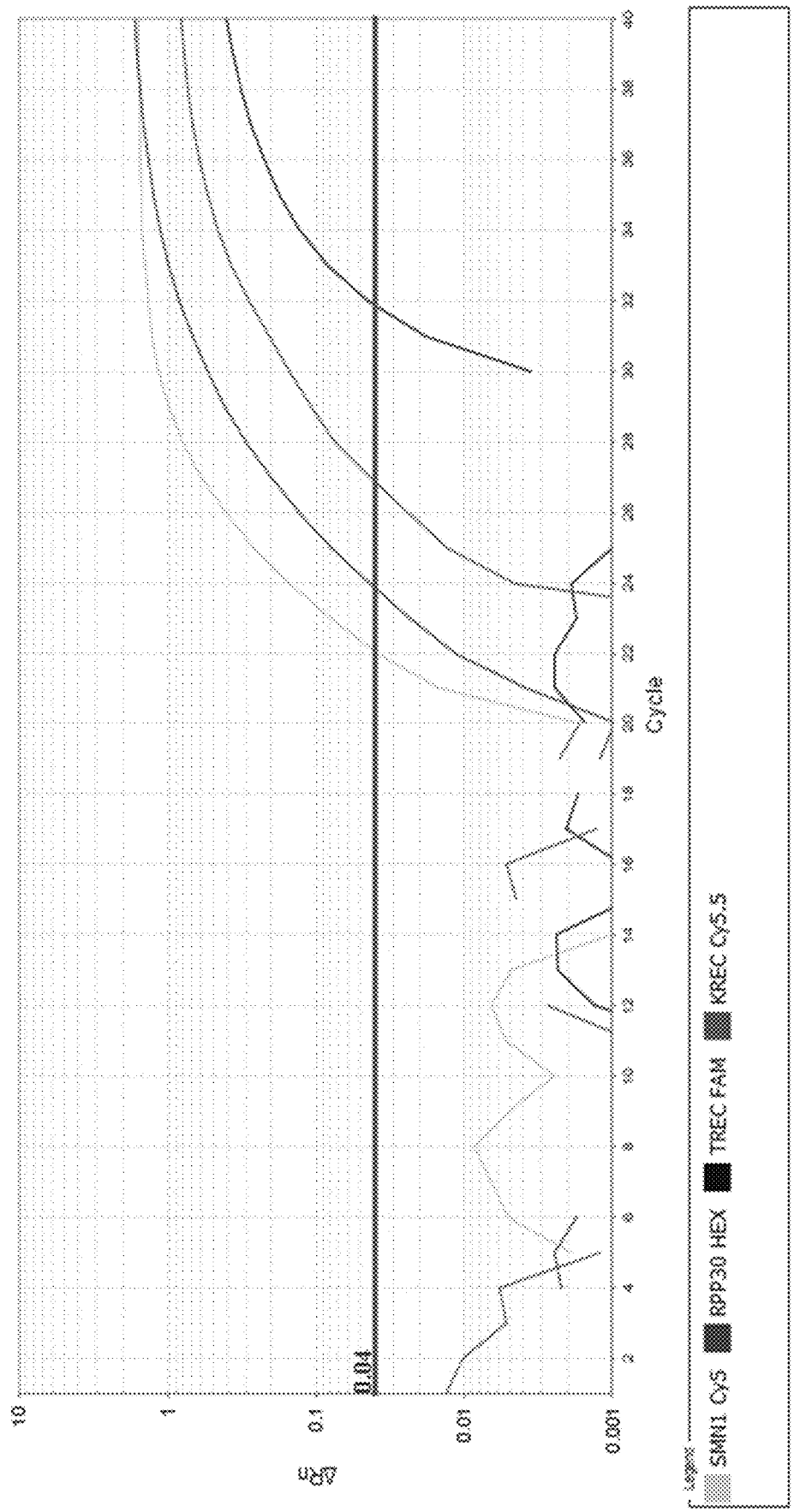
FIG. 1 is a graph showing polymerase chain reaction (PCR) amplification curves for gene targets in a biological sample.

FIG. 1 is a graph showing example qPCR amplification curves obtained by performing the NeoMDX™ qPCR assay on a sample taken from a "normal" newborn infant. In FIG. 1, each of the target genes was amplified, along with the RPP30 control gene, and each amplified gene was separately detected based on fluorescence emission from its corresponding conjugated dye.

However, it has been discovered while performing the NeoMDX qPCR assay on a variety of samples that, in some trials, cross-talk in the Cy5.5 spectral channel due to fluorescence emission from Cy5 can occur, which impairs accurate quantification of both SMN1 and KREC gene targets. For example, in certain samples that were KREC negative and also included relatively high concentrations of SMN1 (yielding relatively high intensity fluorescence emission from Cy5), an amplification curve corresponding to emission from Cy5.5 was also measured, even though the KREC signal was relatively low (but above the predefined detection threshold). Since the samples were known to be KREC negative, such results amounted to false positive tests for the KREC target.

Without wishing to be bound by theory, it is believed that the false KREC amplification curve derived from measured Cy5.5 fluorescence emission resulted from cross-talk due to Cy5 into the Cy5.5 spectral emission channel. Specifically, due to the inability of the filter used to spectrally isolate Cy5.5 fluorescence emission from Cy5 fluorescence emission in the QuantStudio™ Dx system used to perform the analysis, some fluorescence emission from Cy5 was falsely detected as Cy5.5 fluorescence emission in the Cy5.5 spectral channel.

Figure 2:
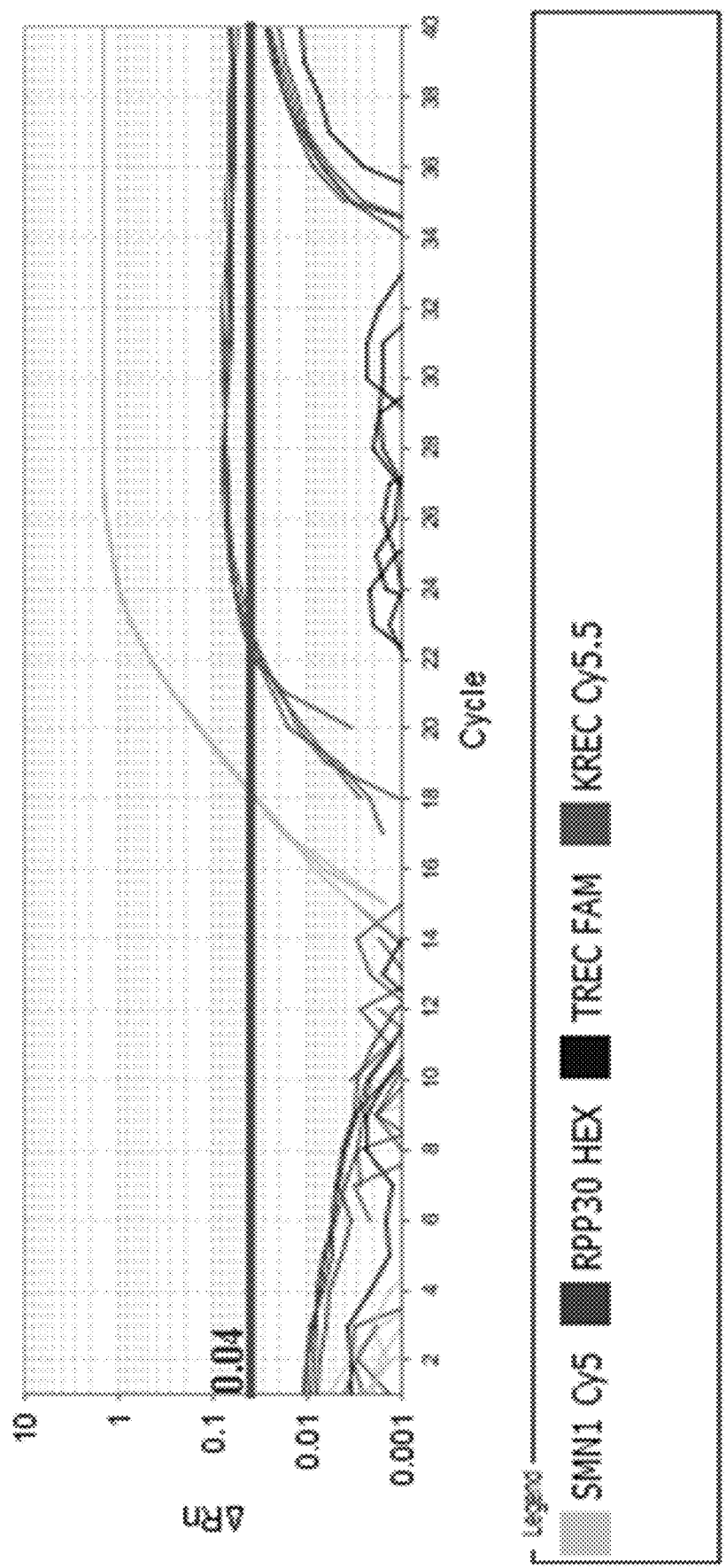
FIG. 2 is a graph showing PCR amplification curves for gene targets in a biological sample, with Cy5 fluorescence emission cross-talk into a spectral emission channel corresponding to Cy5.5.

FIG. 2 is a graph showing example qPCR amplification curves for a KREC negative sample. In FIG. 2, the sample contained $1 \times 10^5$ copies of the SMN1 target gene, but none of the other gene targets from Table 1 (and specifically, no KREC target genes). Nonetheless, a KREC amplification curve was detected based on measured fluorescence emission in the Cy5.5 spectral emission channel (i.e., with the m6 filter in place in the QuantStudio™ Dx system). The fluorescence emission in the Cy5.5 spectral emission channel was due to Cy5 fluorescence emission that was not sufficiently extinguished by the filter associated with the Cy5.5 spectral emission channel to escape detection.

Based on the amplification curves shown in FIG. 2, the sample might be diagnosed as belonging to a patient that is KREC positive, i.e., a "normal" baby. However, a baby with XLA (X-linked Agammaglobulinemia) would display no KREC amplification. Thus, the result shown in FIG. 2 represents a false negative assessment of the patient for XLA.

Effectively, the portion of the Cy5 fluorescence emission signal in FIG. 2 that is detected in the Cy5.5 spectral emission channel functions as "background" against which any "true" Cy5.5 fluorescence emission should be detected to obtain accurate quantitative results for each of the gene targets. For many multispectral analysis systems (including the QuantStudio™ Dx system), before samples are analyzed, the systems are calibrated with "reference" samples to provide the systems with reference spectral information for each of the dyes that are being measured. The reference samples are typically implemented as calibration plates in which some (or all) of the wells in the plate contain reference samples of one of the dyes for which fluorescence emission will be measured. Thus, to calibrate the QuantStudio™ Dx system for measurement of fluorescence emission from each of the dyes in Table 1, a series of multi-well calibration plates is used, where each one of the calibration plates in the series includes wells filled with a different one of the dyes in Table 1. By using only one of the dyes in the wells of each calibration plate, the system measures "pure" reference spectra for that dye at each well location. To complete the calibration, calibration plates filled with a different one of the dyes that will be measured are processed through the system in succession, so that the system is provided with pure reference spectra for each of the dyes.

However, the inventors have discovered that by mixing multiple dyes together in the wells of a single calibration plate, reference spectra are provided to the system that contain contributions from each of the dyes in the plate. These reference spectra are not pure spectra of any one of the dyes. Instead, they contain contributions from each dye in the plate, and are effectively "mixed" reference spectra. Moreover, it has been observed that such mixed reference spectra significantly improve the quantitative analysis of fluorescence emission from the dyes, even when substantial fluorescence emission from one dye is detected in the spectral emission channel of another dye.

As an example, a number of different calibration formulations were tested for the Cy5 calibration plate used in the analysis described above and shown in FIG. 2. In particular, each formulation contained different ratios of Cy5- and Cy5.5-labeled oligonucleotides, with the same calibration buffer. The QuantStudio™ Dx system was calibrated with each of the different formulations, and then the same data file that was generated from the sample containing $1 \times 10^5$ copies of the SMN1 target gene (and none of the other target genes shown in Table 1) was analyzed with according to calibrations defined by each of the different formulations.

By calibrating the system for Cy5 fluorescence emission using a calibration formulation that included both Cy5 and Cy5.5, it was generally observed that fluorescence emission cross-talk from Cy5 fluorescence emission into the Cy5.5 spectral emission channel was reduced. During testing, a formulation that included about 95% Cy5-labeled oligonucleotide and about 5% Cy5.5-labeled oligonucleotide was found to provide a significant reduction in fluorescence emission cross-talk into the Cy5.5 spectral emission channel. The Cy5 and Cy5.5 fluorophores were conjugated to the 5' position on the oligonucleotides (sequence AGGGTTT for the Cy5 conjugate, and TCTGCAC for the Cy5.5 conjugate).

The complete formulation of this calibrator was as follows:

TABLE 2

| Amount/Concentration | Component |
|---|---|
| 285 nM | Cy5-labeled oligonucleotide |
| 15 nM | Cy5.5-labeled olignonucleotide |
| 1x | Phosphate buffered saline, pH 7.3-7.5 |
| 0.1% | Tween 20 detergent |
| 0.01% | Antifoam B |
| — | Molecular grade water |

Figure 3:
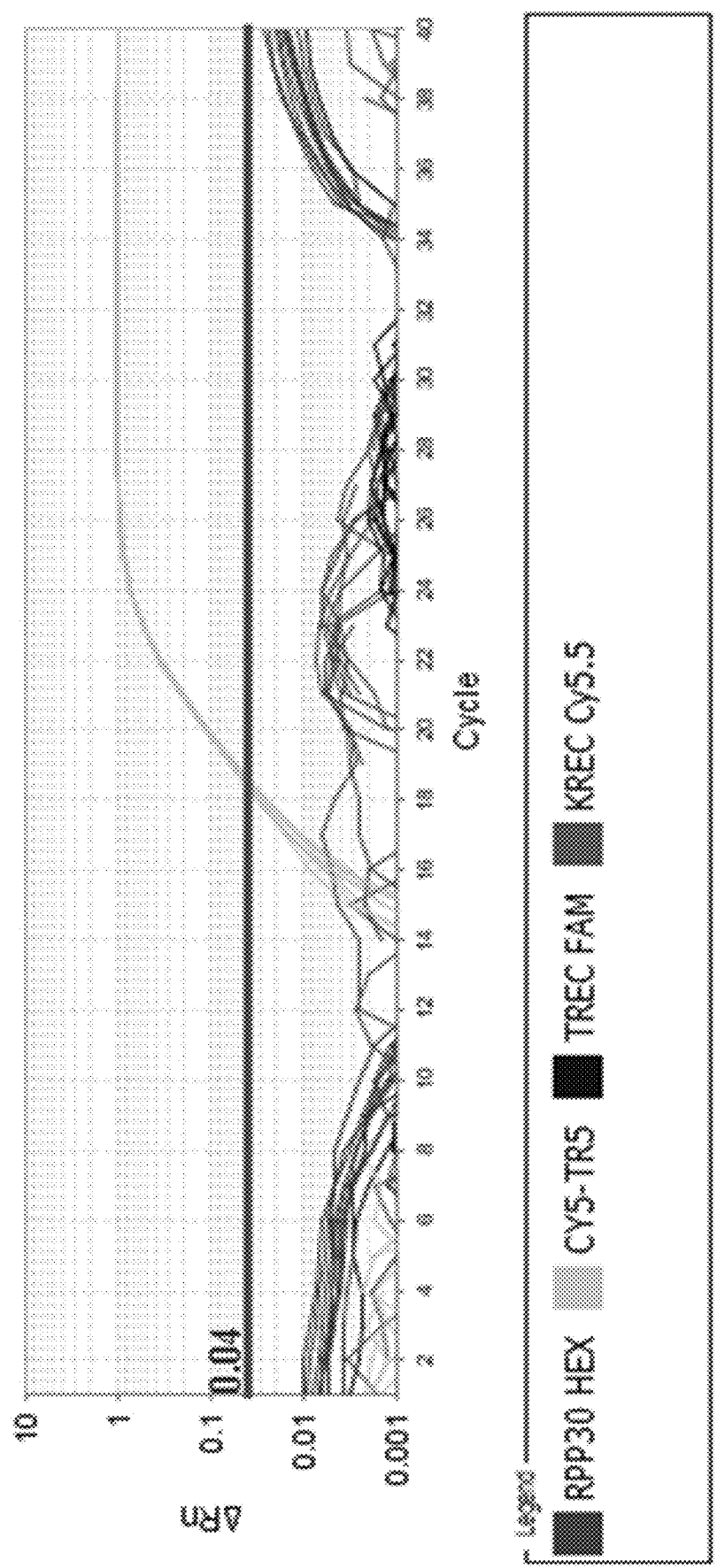
FIG. 3 is a graph showing PCR amplification curves for gene targets in a biological sample, measured using a multispectral analysis system calibrated with a calibration formulation that included both Cy5 and Cy5.5.

FIG. 3 is a schematic diagram showing qPCR amplification curves for a sample analyzed following calibration of the QuantStudio™ Dx system with the calibrator formulation shown in Table 2. As described above, the sample contained $1 \times 10^5$ copies of the SMN1 target gene, and none of the other target genes shown in Table 1. In particular, in FIG. 3, KREC amplification is not observed, consistent with the absence of KREC in the sample and, effectively, the elimination of Cy5 fluorescence emission cross-talk into the Cy5.5 spectral emission channel.

Experiments with several different calibrator formulations resulted in a reduction of Cy5 fluorescence emission cross-talk into the Cy5.5 spectral emission channel. In general, it was observed that cross-talk was reduced when the concentration of Cy5.5 relative to the total concentration of Cy5 and Cy5.5 in the calibrator formulation was greater than zero (e.g., 0.001 or more, 0.002 or more, 0.005 or more, 0.01 or more, 0.02 or more, 0.03 or more, 0.04 or more, 0.05 or more, 0.06 or more, 0.07 or more, 0.08 or more, 0.09 or more, 0.10 or more, 0.12 or more, 0.14 or more, 0.16 or more, 0.18 or more, 0.20 or more, 0.25 or more). In some embodiments, it was observed that an over-correction for Cy5 fluorescence emission cross-talk into the Cy5.5 spectral emission channel occurred when the concentration of Cy5.5 relative to the total concentration of Cy5 and Cy5.5 in the calibrator formulation was greater than 0.10.

Figure 4:
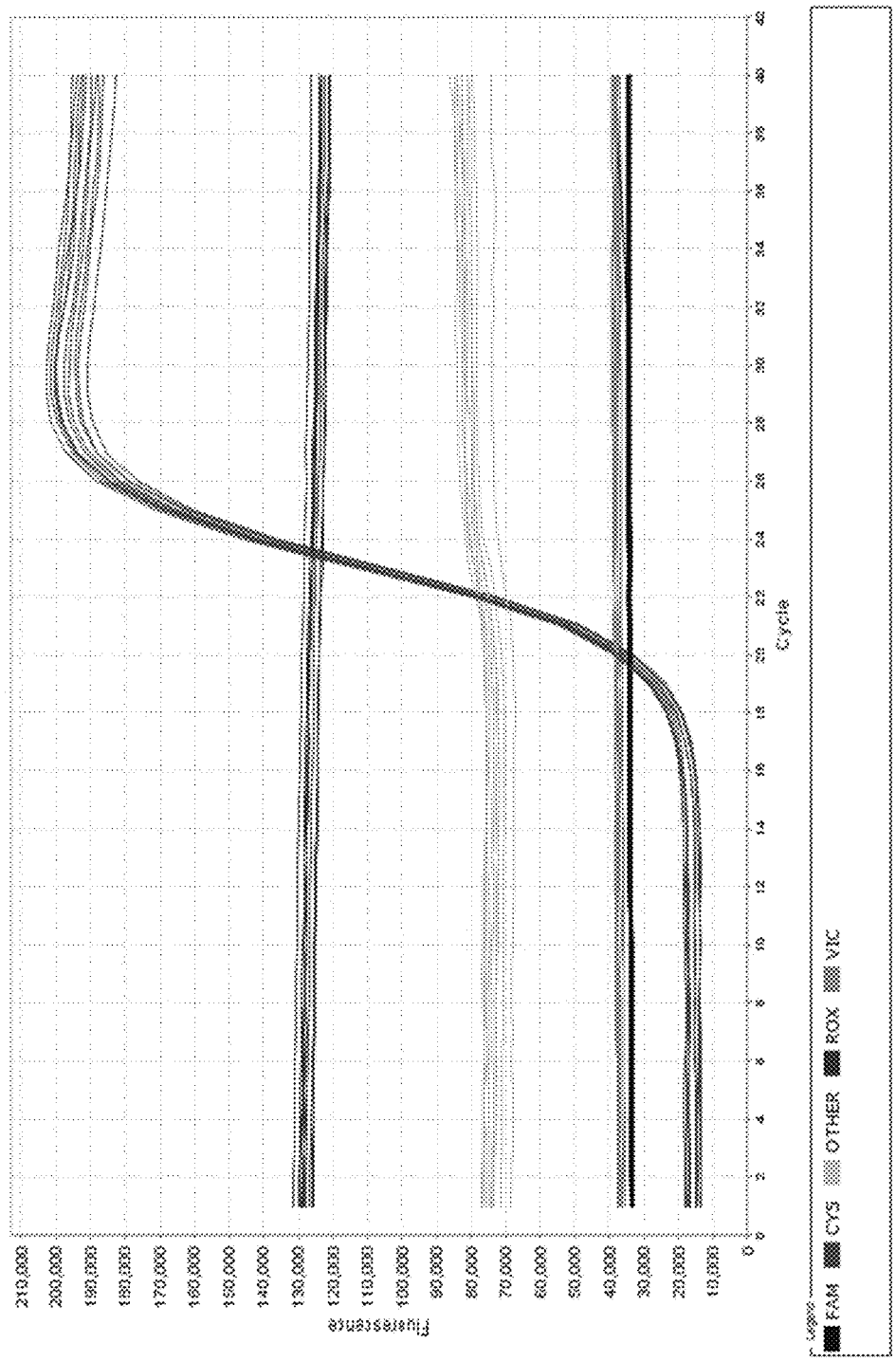
FIG. 4 is a graph showing PCR amplification curves for gene targets in a biological sample, measured using a multispectral analysis system calibrated with a calibration formulation that included only Cy5.
Figure 5:
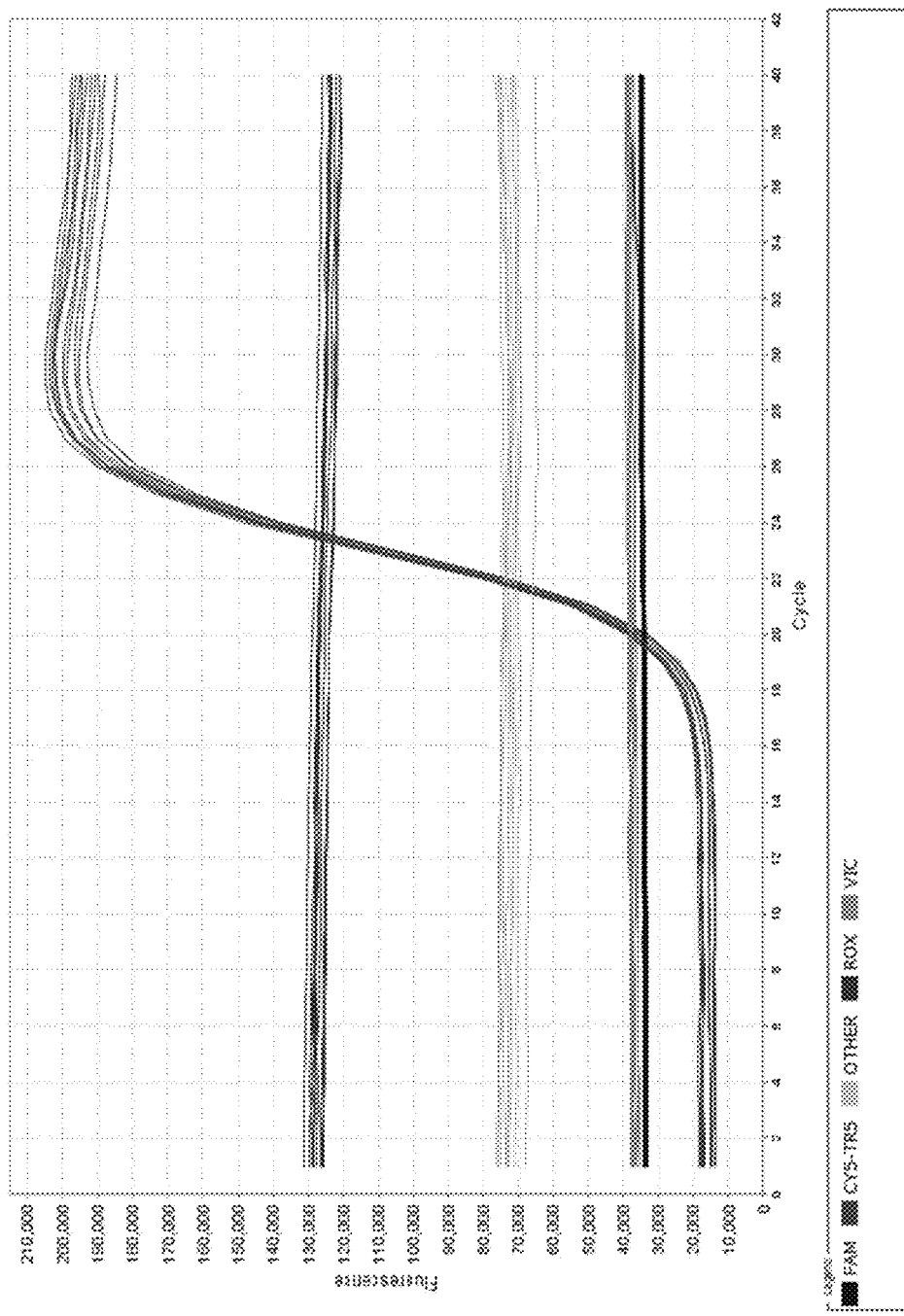
FIG. 5 is a graph showing PCR amplification curves for gene targets in a biological sample, measured using a multispectral analysis system calibrated with a calibration formulation that included a dye mixture of 5% Cy5.5 and 95% Cy5.
Figure 6:
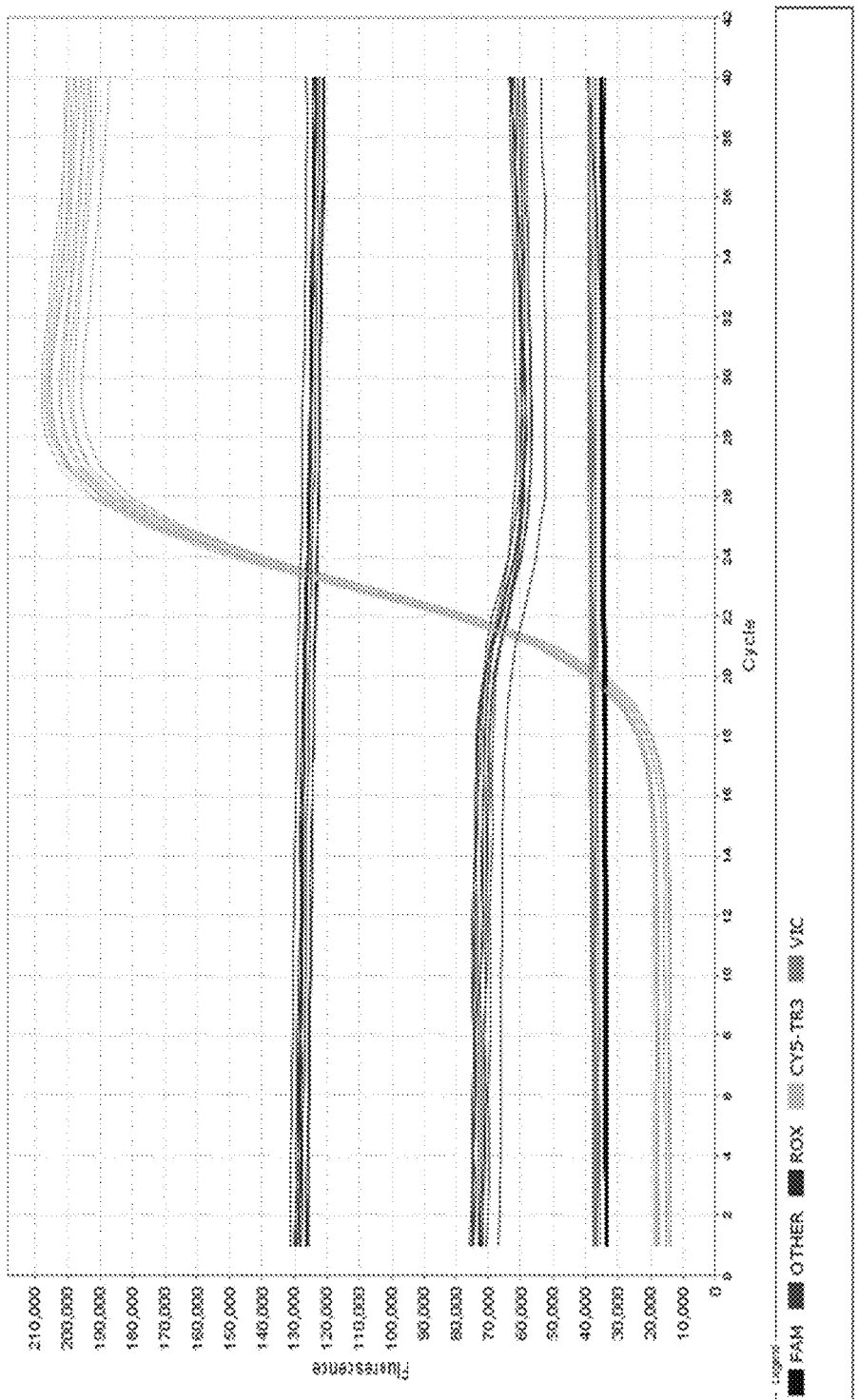
FIG. 6 is a graph showing PCR amplification curves for gene targets in a biological sample, measured using a multispectral analysis system calibrated with a calibration formulation that included a dye mixture of 10% Cy5.5 and 90% Cy5.

To determine which relative concentration of Cy5.5 in the prepared calibrators yielded the optimum correction for Cy5 fluorescence emission cross-talk, a set of calibrators were prepared with different relative concentrations of Cy5- and Cy5.5-conjugated oligonucleotides, and the other components listed in Table 2. Each of these calibrators was used to calibrate the QuantStudio™ Dx system, after which the same sample described above was analyzed by the system. FIGS. 4, 5, and 6 show qPCR amplification curves for the sample after calibration of the system with calibrators that contained 0% Cy5.5-labeled oligonucleotide, 5% Cy5.5-labeled oligonucleotide, and 10% Cy5.5-labeled oligonucleotide, respectively. The amplification curves corresponding to the Cy5.5-labeled oligonucleotides are labeled "Other" in the figure legends.

To assess whether each calibrator yielded amplification curves that were undercorrected (e.g., still showed some cross-talk), overcorrected, or ideally corrected, the flatness of the multicomponent amplification curve over 40 PCR amplification cycles was used as a metric. In general, it was assumed that the flatter the multicomponent amplification curve, the closer that correction was to being ideal.

Figure 7:
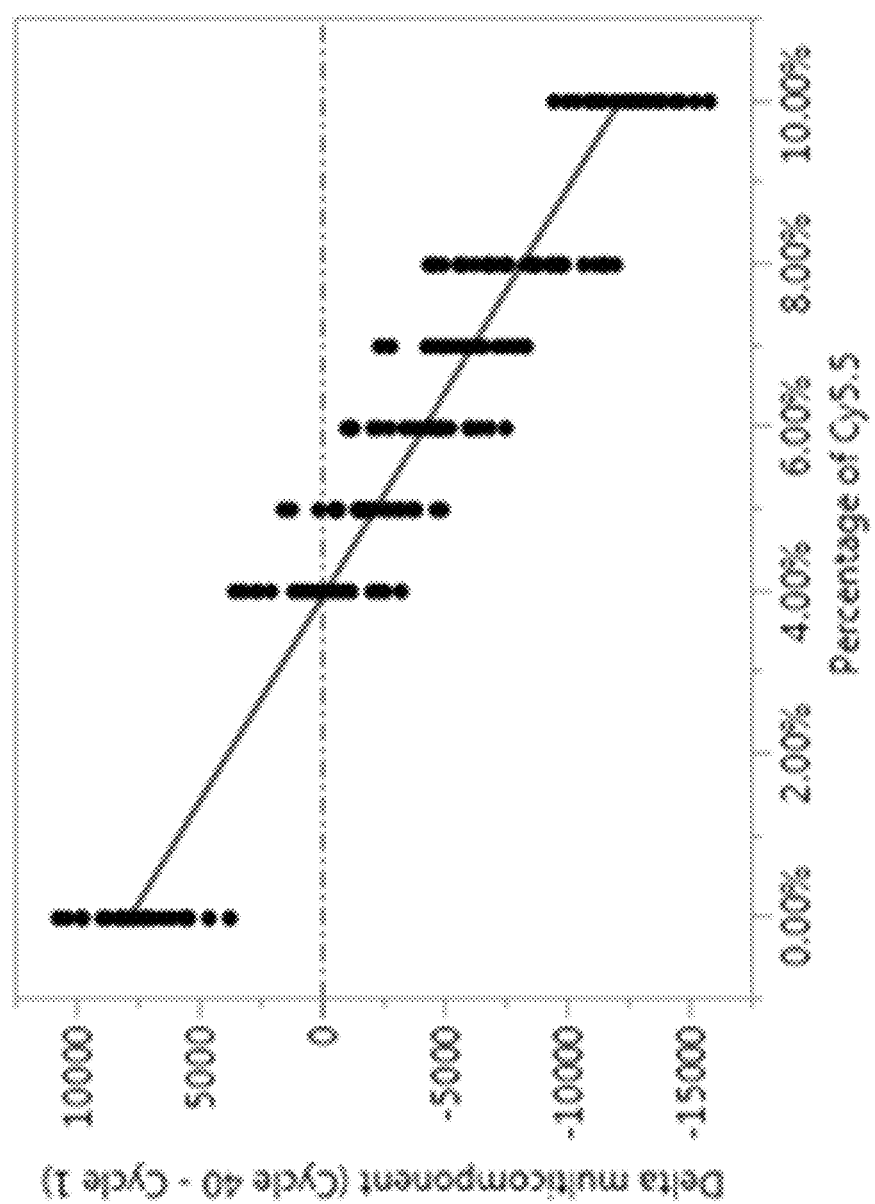
FIG. 7 is a graph showing the deviation of a multicomponent PCR amplification curve from a constant fluorescence intensity, measured using a multispectral analysis system calibrated with a calibration formulation that include a dye mixture of Cy5.5 and Cy5, as a function of the percentage of Cy5.5 in the dye mixture.
Figure 8:
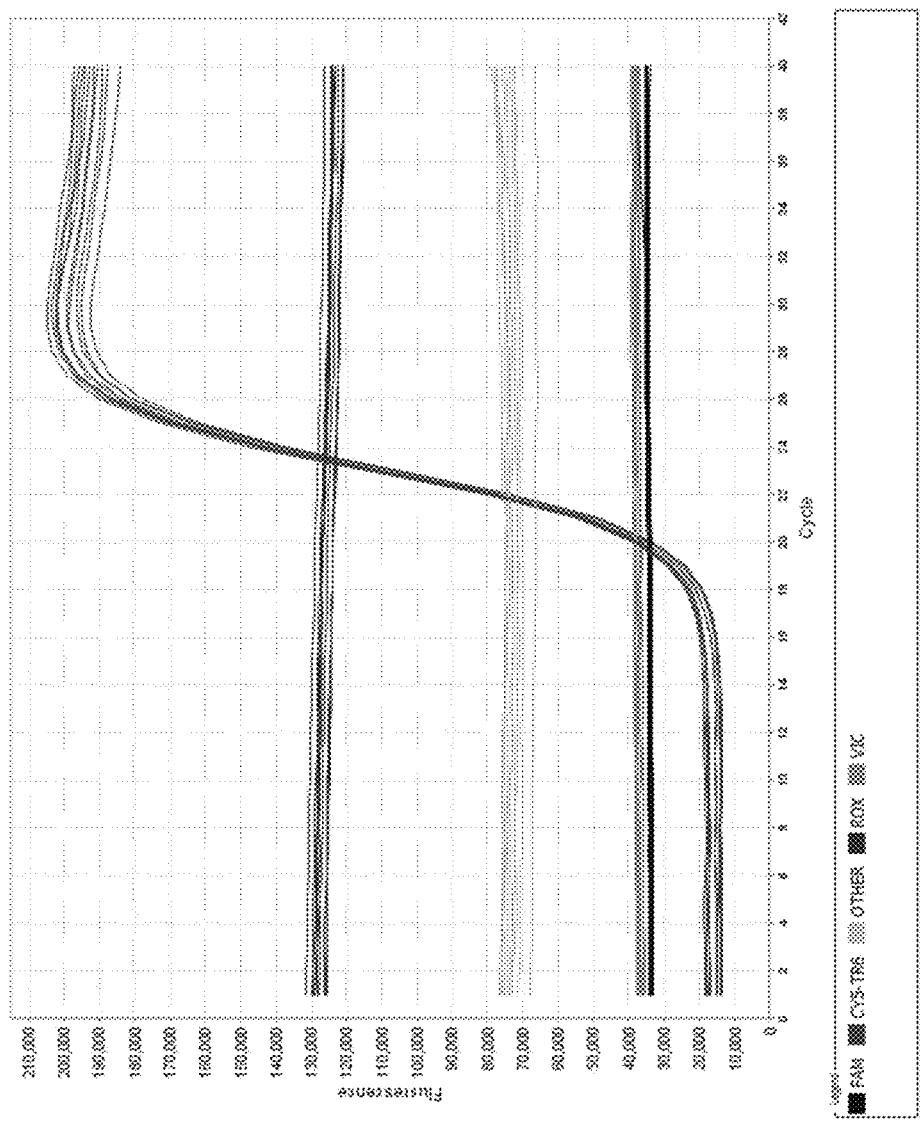
FIG. 8 is a graph showing PCR amplification curves for gene targets in a biological sample, measured using a multispectral analysis system calibrated with a calibration formulation that included a dye mixture of 4% Cy5.5 and 96% Cy5.

FIG. 7 is a graph showing the change in the multicomponent amplification curve fluorescence intensity as a function of the percentage of Cy5.5-labeled oligonucleotide in the calibrator used to calibrate the system prior to measuring each multicomponent amplification curve. In FIG. 7, results fall generally along a straight line, which is confirmed by the regression analysis shown in the figure. The regression analysis predicts that a calibrator prepared with approximately 4% Cy5.5-labeled oligonucleotide (and approximately 96% Cy5-labeled oligonucleotide) yields the best compensation for Cy5 fluorescence emission into the Cy5.5 spectral emission channel. qPCR amplification curves (including the multicomponent curve) obtained after calibrating the system with the calibrator prepared with approximately 4% Cy5.5-labeled oligonucleotide and approximately 96% Cy5-labeled oligonucleotide are shown in the graph in FIG. 8.

While the foregoing examples of calibrator formulations specifically involve mixtures of Cy5 and Cy5.5 to reduce or eliminate fluorescence emission cross-talk, similar principles apply to mixtures of any two fluorophores used in calibration formulations to reduce cross-talk in spectral emission channels. For example, consider the more general situation where two spectral contributors (fluorescent dyes, endogenous fluorophores, expressed fluorescent moieties) A and B each exhibit fluorescence emission such that at least some fluorescence emission from A is detected in the spectral emission channel of B, due to the inability of the detection system to fully separate the emission from A and B (e.g., using filters).

To calibrate the multispectral analysis system to properly correct for this cross-talk, a calibrator can be prepared that includes a relatively large fraction of A and a relatively smaller, but non-zero, fraction of B, as a mixture. The mixture is then used to calibrate the system for detection of fluorescence emission from A. In general, the fraction of B in the calibration formulation relative to the total amount of A and B in the formulation can be 0.001 or more (e.g., 0.002 or more, 0.003 or more, 0.004 or more, 0.005 or more, 0.01 or more, 0.02 or more, 0.025 or more, 0.03 or more, 0.035 or more, 0.04 or more, 0.045 or more, 0.05 or more, 0.055 or more, 0.06 or more, 0.065 or more, 0.07 or more, 0.08 or more, 0.09 or more, 0.10 or more, 0.12 or more, 0.14 or more, 0.16 or more, 0.18 or more, 0.20 or more, 0.25 or more).

A variety of different calibrators (corresponding to different pairs of fluorophores A and B can be prepared according to the methods disclosed herein. In general, calibrators can include one or more dyes. Suitable dyes for use in calibrators can include (but are not limited to) one or more rhodamine-based dyes such as ROX™, TAMRA™, and Texas Red® (rhodamines, carboxyrhodamines, methylrhodamines, and derivatives thereof), one or more fluorescein-based dyes such as FAM™, VIC®, SIMA™, TET™, and HEX™ (fluoresceins, carboxyfluoresceins, chlorofluoresceins, and derivatives thereof), one or more cyanine-based dyes (e.g., cyanine, and derivatives thereof) such as Cy3, Cy3.5, Cy5, and Cy5.5, and one or more xanthene-based dyes such as JOE™

Examples of pairs of fluorophores A and B (in addition to Cy5 and Cy5.5) include, but are not limited to: TAMRA™ and HEX™; FAM™ and HEX™, FAM™ and SIMA™, HEX™ and Cy3, SIMA and Cy3, Cy3 and Cy3.5; Cy3 and ROX™; Cy3.5 and Cy5; and ROX™ and Cy5.

In some embodiments, mutual cross-talk can occur between the spectral emission channels of fluorophores A and B. In other words, some fluorescence emission from A can be observed in the spectral emission channel of B, and some fluorescence emission from B can be observed in the spectral emission channel of A. To correct for such spectral cross-talk, the system can be calibrated to detect fluorescence emission from A with a first calibrator that includes concentrations of both A and B, with the concentration of A being larger than the concentration of B in the first calibrator. The system can also be calibrated to detect fluorescence emission from B with a second calibrator that includes concentrations of both A and B, with the concentration of B being larger than the concentration of A in the second calibrator.

In general, the relative concentrations of A and B in the first and second calibrators can be selected as desired to provide sufficient correction for spectral cross-talk. In some embodiments, for example, the first calibrator can have a composition similar to the compositions discussed above. Further, in certain embodiments for example, the second calibrator can have a composition in which the fraction of A in the calibration formulation relative to the total amount of A and B in the formulation can be 0.001 or more (e.g., 0.002 or more, 0.003 or more, 0.004 or more, 0.005 or more, 0.01 or more, 0.02 or more, 0.025 or more, 0.03 or more, 0.035 or more, 0.04 or more, 0.045 or more, 0.05 or more, 0.055 or more, 0.06 or more, 0.065 or more, 0.07 or more, 0.08 or more, 0.09 or more, 0.10 or more, 0.12 or more, 0.14 or more, 0.16 or more, 0.18 or more, 0.20 or more, 0.25 or more).

While the foregoing discussion has focused on calibrators that provide for correction when two different spectral contributors A and B exhibit fluorescence emission crosstalk, more complex calibrators can also be prepared for situations when cross-talk occurs among more than two spectral contributions. For example, in situations where fluorescence emission from spectral contributors A and B is detected in the spectral emission channel for spectral contributor C, the multispectral analysis system can be calibrated with calibration formulations that include mixtures of A, B, and C. For example, the system can be calibrated to detect fluorescence emission from A with a calibration formulation that includes a relatively high fraction of A and a relatively low fraction of C (similar to the low fractions of A and B discussed above), and calibrated to detect fluorescence emission from B with a calibration formulation that includes a relatively high fraction of B and relatively low fraction of C (similar to the low fractions of A and B discussed above). The fractions of A, B, and C in the various calibration formulations can vary as desired to achieve suitable compensation for fluorescence emission cross-talk.

Similarly, where fluorescence emission from a spectral contributor A is observed in spectral emission channels for spectral contributors B and C, the multispectral analysis system can be calibrated to detect fluorescence emission from A with a calibration formulation that includes a relatively high fraction of A and relatively low fractions of B and C (similar to the low fractions of A and B discussed above).

More generally, the calibration formulations disclosed herein can include combinations of two, three, four, five, or even more than five spectral contributors (fluorophores such as dyes, endogenous fluorescent entities, and expressed fluorescent moieties), used to calibrate multispectral analysis systems to compensate for fluorescence emission cross-talk by one or more of the spectral contributors into spectral emission channels corresponding to one or more of the other spectral contributors.

While specific examples of fluorophores (or spectral contributors) A and B have been described above, more generally, the methods and calibrators described herein can be used in any circumstance in which fluorescence from one spectral contributor (e.g., B) is detected in a spectral wavelength band dedicated to the measurement of fluorescence emission from another spectral contributor (e.g., A). For example, where a sample includes spectral contributors A and B, and fluorescence from contributor A is measured in a wavelength band centered at wavelength $\lambda_A$, then mixtures of A and B can be used in calibrators if the total fluorescence intensity of spectral contributor B in the wavelength band centered at $\lambda_A$ is, for example, 1% or more (e.g., 2% or more, 3% or more, 5% or more, 7% or more, 10% or more, 15% or more, 20% or more, 25% or more, 30% or more, 40% or more, 50% or more) of the fluorescence intensity of spectral contributor A at wavelength $\lambda_A$. Similar considerations apply for spectral interference (i.e., cross-talk) among more than two spectral contributors.

Figure 9:
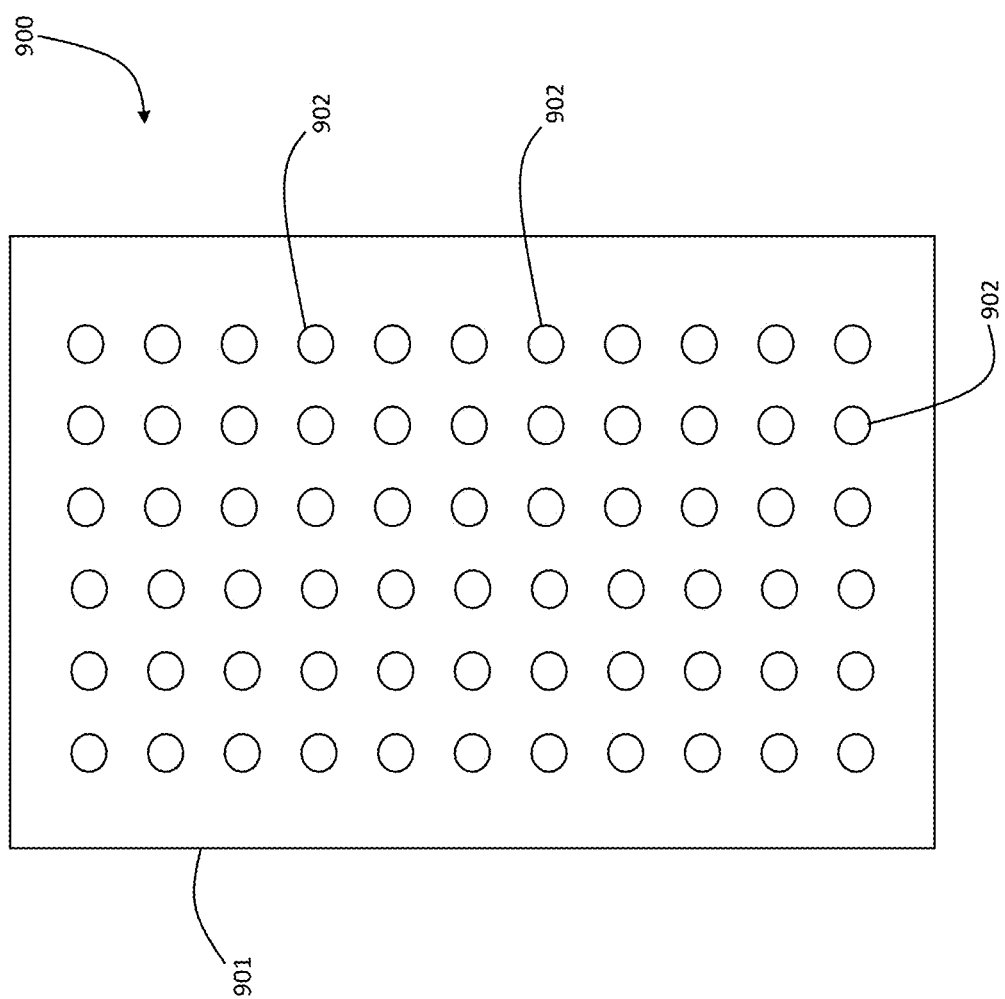
FIG. 9 is a schematic diagram of an example of a calibration sample.

FIG. 9 is a schematic diagram showing an example of a calibration sample 900. Sample 900 includes a substrate 901 (e.g., a plate, a slide, a wafer, a block) with a plurality of calibration regions 902. Calibration regions 902 can be formed on substrate 901 in various ways. In some embodiments, for example, calibration regions 902 are simply defined areas on the surface of substrate 901. In certain embodiments, calibration regions 902 correspond to recesses (i.e., wells) formed in the surface of substrate 901. In some embodiments, calibration regions 902 can correspond to protrusions, extensions, or other raised structures that extend outward from the surface of substrate 901.

In general, calibration sample 900 can include any number of calibration regions 902. For example, the number of calibration regions 902 can be 10 or more (e.g., 20 or more, 50 or more, 100 or more, 200 or more, 300 or more, 400 or more, 500 or more, 700 or more, 1000 or more, or even more).

Calibration sample 900 includes a calibrator—which corresponds to a mixture of reagents, including one or more fluorophores—in one or more of the calibration regions 902. As described above, the calibrator in one or more of the calibration regions can include mixtures of fluorophores (e.g., fluorophores A and B) with emission spectra that are relatively close spectrally, such that emission from one of the fluorophores is detected in a spectral band dedicated to the other fluorophore.

In some embodiments, a set of calibration samples can be provided to accompany an assay that features multiple dyes, each of which functions as a spectral reporter for a specific molecular target in a sample. For example, in an assay that includes dyes A, B, C, D, and E, a set of 5 calibration samples can be provided, one or for each of the 5 dyes in the assay. If, for example, dyes C, D, and E are measured in distinct spectral bands with no cross-talk from any of the other dyes, then the calibration samples corresponding to dyes C, D, and E can each include only one dye (i.e., dyes C, D, and E, respectively) at each of the calibration regions.

If a non-negligible amount of fluorescence from dye A is measured in the spectral band dedicated to the measurement of dye B, then the calibration sample for dye B can include a mixture of mostly dye B and a relatively small amount of dye A at each of the calibration regions 902, as described above.

If a non-negligible amount of fluorescence from dye B is measured in the spectral band dedicated to the measurement of dye A, then the calibration sample for dye A can include a mixture of mostly dye A and a relatively small amount of dye B at each of the calibration regions 902, as described above. Alternatively, if no appreciable amount of fluorescence from dye B is measured in the spectral band dedicated to the measurement of dye A, then the calibration sample for dye A can include only dye A at each of the calibration regions 902.

In general, for an assay with N fluorescent dyes that are measured independently, N calibration samples can be provided. For each particular calibration sample (corresponding to a dye M) in the set of N samples, the calibration regions 902 can each include a relatively large proportion of the dye M that nominally corresponds to that sample, and relatively small proportions of any other dyes that exhibit measurable fluorescence in the spectral detection band that is dedicated to the measurement of dye M, as discussed above.

Figure 10:
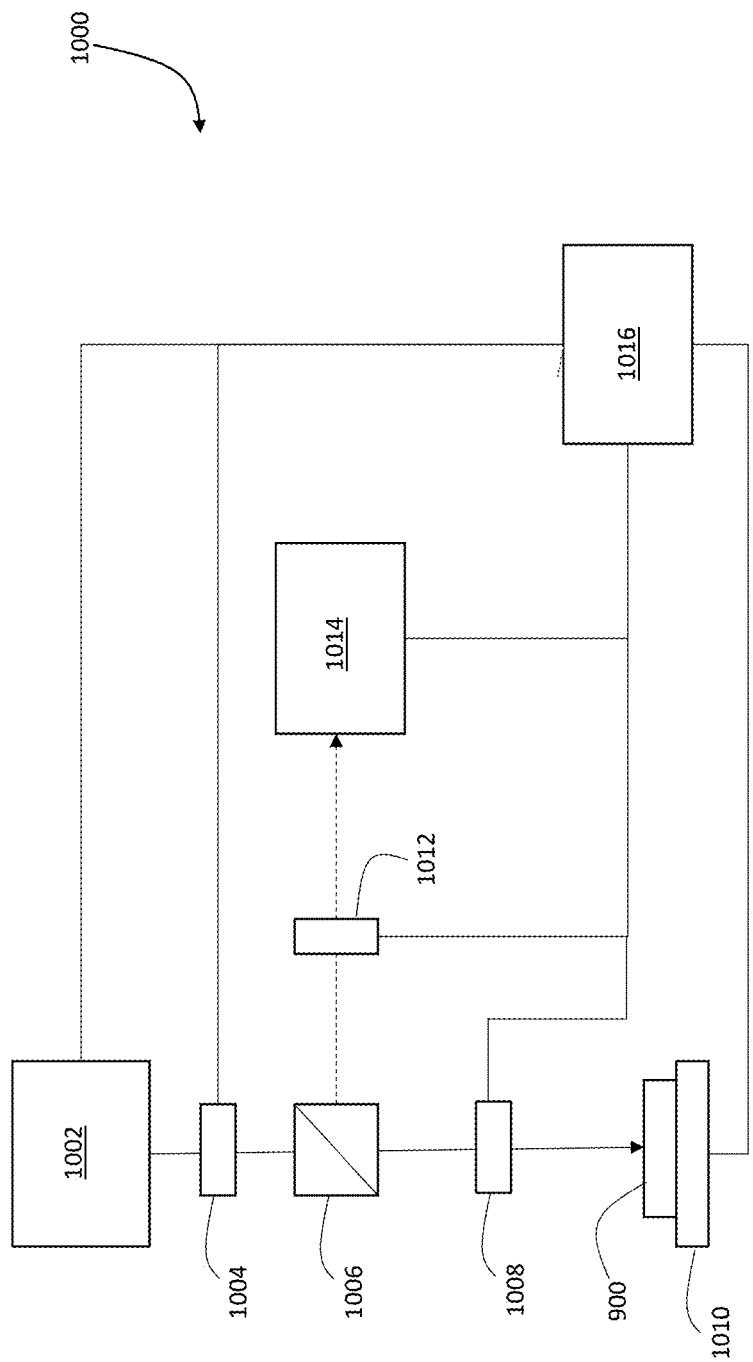
FIG. 10 is a schematic diagram of an example of a multispectral analysis system.

The calibration samples described can be used to calibrate a variety of different multispectral analysis systems. An example of one such system is the QuantStudio™ Dx system. More generally, FIG. 10 shows an example of a multispectral analysis system 1000 that can be calibrated with the calibration samples described. System 1000 includes a radiation source 1002, an emission filter 1004, a beam splitter 906, beam optics 1008, a sample stage 1010, an emission filter 1012, and a detector 1014. The source, filters, and detector are connected to controller 1016 which transmits control signals to these components, and receives reporting signals and measurement information from the components.

To calibrate system 1000, a calibration sample 900—which is dimensioned to be received by system 1000 (and specifically, on stage 1010) is positioned on the stage. Calibration sample 900 corresponds to a particular dye M, and controller 1016 adjusts emission filter 1012 to select a spectral band (i.e., a "spectral channel") in filter 1012 that is dedicated to the measurement of fluorescence emission from dye M.

Radiation source 1002 then directs incident radiation through filter 1004, beam splitter 1006, and beam optics 1008, and onto calibration sample 900. The incident radiation excites the calibrator in calibration regions 902, causing the calibrator to emit fluorescence. The emitted fluorescence passes through beam optics 1008, is reflected by beam splitter 1006, passes through emission filter 1012, and is detected by detector 1014.

Detector 1014 measures fluorescence emission from each of the calibration regions 902, and transmits the fluorescence emission measurements to controller 1016. Controller 1016 then uses the measured fluorescence emission information to calibrate each of the calibration regions 902 for fluorescence measurements of dye M. The specific manner in which each of the calibration regions 902 are calibrated can vary widely. In some embodiments, for example, the spectrally-resolved measured fluorescence emission information forms a "baseline" measurement signal against which fluorescence emission measurements from samples are normalized, or which is subtracted from fluorescence emission measurements from samples. In certain embodiments, the spectrally-resolved measured fluorescence emission information from the calibrators forms an effective eigenspectrum or pure spectrum corresponding to dye M, which is then used to quantify measured fluorescence information from the dye M in samples. The measured fluorescence information from the calibrators of calibration sample 900 can also be used in a wide variety of other calibration techniques.

To complete the calibration of system 1000, controller 1016 cycles through each of the dyes used in a corresponding assay in turn, for each dye adjusting emission filter 1012 to select a spectral band dedicated to measurement of fluorescence emission from the dye, and then measuring fluorescence emission from each calibration region 902 on a calibration sample 900 positioned on stage 1010 and corresponding to the dye. The measured fluorescence information from the calibration sample 900 corresponding to each dye is then used to calibrate system 1000 to measure fluorescence emission from that dye in samples. The calibration information can be stored in a storage unit, for example, connected to controller 1016.

When system 1000 has been calibrated, the system can be used to measure fluorescence emission from each of the dyes in an assay that is performed on a sample. For example, if a sample is prepared with an assay that includes N dyes, then fluorescence emission measurements corresponding to each of the N dyes are performed sequentially, with controller 1016 adjusting emission filter 1012 to select a spectral measurement band corresponding to each dye in turn, as in the calibration procedure described above.

Raw fluorescence emission measurements for each dye in the assay can be corrected using the stored calibration information, which permits quantitative information to be obtained. For example, in an assay with multiple dyes, each of which functions as a spectral reporter for a particular gene target in a sample, each of the gene targets can be identified based on the corrected measured fluorescence emission information for the corresponding dyes, and expression of each of the gene targets in the sample can be quantified.

Hardware and Software Implementation

In general, controller 1016 can be configured to perform any of the control, calibration, or data analysis functions described herein. These functions can be performed entirely by controller 1016 (e.g., autonomously), or a set of functions or steps can be performed by part by controller 1016 and in part by a user of system 1000. When performed fully or partly by controller 1016, the functions can be implemented in computer programs using standard programming techniques. Such programs are designed to execute on programmable computers, dedicated controllers, or specifically designed integrated circuits, each comprising an electronic processor (e.g., an electronic processor in controller 1016), a data storage system (including memory and/or storage elements), at least one input device, and least one output device, such as a display. Each computer program can be implemented in a high-level procedural or object-oriented programming language, or an assembly or machine language. Furthermore, the language can be a compiled or interpreted language. Each such computer program can be stored on a computer readable storage medium (e.g., a magnetic storage medium such as a hard drive, an optical storage medium such as a CD-ROM or DVD, a persistent solid state storage medium such as a solid state hard drive) that, when read by a device with a processor, can cause the processor in the device to perform the control and analysis functions described herein.

Examples

To investigate the performance of calibration samples with mixtures of two dyes from a single assay, studies were performed to determine three quantities relating to measurement limits for assay targets. The Limit of Blank (LoB) is the highest measurement result that is likely to be observed (with a stated probability [$\alpha$]) for a blank sample, that contains no analyte. It defines the variation of the background or the zero sample. The Limit of Detection is the measured quantity value, obtained by a given measurement procedure, for which the probability of falsely claiming the absence of a measurand in a material is $\beta$, given a probability $\alpha$ of falsely claiming its presence. For molecular measurement procedures which differ from typical measurement procedures because all blank or negative sample results normally are reported as negative, the LoD is calculated from a probit regression model as the measurand concentration at which, with a predefined probability (usually 95%), measurement results yield a positive classification. The Limit of Quantification (LoQ) is the lowest amount of a measurand in a material that can be quantitatively determined with state accuracy (as total error or as independent requirements for bias and precision) under stated experimental conditions. LoQ may be defined based on functional sensitivity or based upon total error.

Studies were performed to determine: (1) the LoB for all the analytes targeted by an assay (the "LoB study"); (2) the LoD for two semi-quantitative analytes, sjTREC and KREC, targeted by an assay (the "LoD" study); and (3) the LoQ for the same two semi-quantitative analytes, sjTREC and KREC, targeted by the assay (the "LoQ" study). The assay was the NeoMDx assay, and the LoD and LoQ for two germline targets (SMN1 and RPP30) of the assay were not evaluated.

The LoB study was performed with contrived analyte-negative samples which were created by spiking SMN1-negative cells (obtained from Coriell Institute for Medical Research, Camden, NJ) into leukocyte-depleted human blood. The Coriell cell line, which is also sjTREC- and KREC-negative naturally, was added at a target of 30,000 genome-copies/µL, a concentration typical for a neonate. Five individual contrived analyte-negative samples (CANS1-5) were prepared by spiking the Coriell cell line into five different lots of leukocyte-depleted human blood.

The five lots of leukocyte-depleted human blood (obtained from Zen-Bio, Research Triangle Park, NC) were washed three times with saline solution and the hematocrit adjusted to 40-55% (Table 3). The Coriell SMA cells were cultured in a RPMI medium supplemented with FBS and penicillin/streptomycin. The cells were counted using a Cell Countess instrument (Thermo Fisher, Waltham, MA).

Approximately 15000 cells were spiked per microliter of leukocyte-depleted human blood to obtain the contrived analyte-negative samples. After dispensing the prepared blood on filter paper, the DBS samples were dried overnight and then stored at −30° C. to −16° C. in a sealed bag with desiccant until use. Table 3 describes the samples used to determine LoB.

TABLE 3

| Sample name | Hematocrit (%) | Lot# of Leukocyte Depleted Blood |
|---|---|---|
| CANS1 | 49.2 | W36981900271000 |
| CANS2 | 49.8 | W36981900281900 |
| CANS3 | 49.5 | W36981900270800 |
| CANS4 | 50.0 | W36981900281700 |
| CANS5 | 49.5 | W36981900270500 |

As the cell line contained a normal level of RPP30, the contrived analyte-negative samples were not suitable to establish the LoB of the RPP30 target, but suitable for the other three analytes, sjTREC, KREC and SMN1.

For the LoD and LoQ studies, due to the rarity of research specimens for the SCID and XLA disorders, it was challenging to find representative newborn DBS samples that happen to have sjTREC and KREC at desired levels. Therefore, the studies were conducted using contrived samples. The contrived samples were prepared by diluting cord blood with adult whole blood or with leucocyte-depleted human red blood that has sjTREC and/or KREC levels undetectable by the assay. HL-60 cells were spiked into the adult whole blood or leucocyte-depleted blood to adjust the RPP30 Ct values to match the RPP30 Ct value in cord blood (within 1 Ct difference).

First, the initial values of sjTREC and KREC (copies/μL blood) in each cord blood was assigned by testing against a 5-level (250, 500, 1000, 3000, 10000 copies/μL blood) standard curve generated using DBS samples containing serial dilutions of ddPCR-quantified linearized TREC, KREC, SMN1 and RPP30 plasmids in leucocyte-depleted human blood. The results are summarized in Table 4.

TABLE 4

| Blood | Lot# | Hematocrit (%) | sjTREC (copies/μL blood) | KREC (copies/μL blood) |
|---|---|---|---|---|
| Cord blood AB+ | ZEN00403 (Lot 1) | 48.2 | 368 | 1132 |
| Cord blood A+ | ZEN00410 (Lot 2) | 47.2 | 492 | 1174 |
| Cord blood O− | ZEN00409 (Lot 3) | 51.9 | 344 | 910 |

Three lots of adult whole blood were then tested to determine their endogenous levels of each analyte to check if they were suitable to be used as the diluent. The mean Ct values of 6 replicates of each adult whole blood are summarized in Table 5.

TABLE 5

| Blood | Lot# | TREC Ct | KREC Ct | SMN1 Ct | RPP30 Ct |
|---|---|---|---|---|---|
| Adult whole blood | W36981900485900 | No Ct | 32.48 | 24.47 | 25.17 |
| Adult whole blood | W36981900296700 | 37.35 | 33.35 | 24.47 | 24.39 |
| Adult whole blood | W36981900297300 | 34.84 | 34.41 | 25.77 | 27.35 |

Although sjTREC are usually low in adult whole blood, two out of the three lots had detectable levels of sjTREC and thus they were replaced by leucocyte-depleted human blood as diluent in the preparation of samples for TREC LoD/LoQ. All three lots of adult whole blood also had detectable levels for KREC so for the preparation of KREC LoD/LoQ samples, leucocyte-depleted human blood was used as a diluent. The diluents used for each cord blood are listed in Table 6. The RPP30 Ct values of the diluents were adjusted to match the cord bloods RPP30 Ct values (within 1 Ct difference) by spiking HL-60 cells into the diluents according to the study design.

TABLE 6

| Analyte name | Cord blood Lot# | Diluent Name | Diluent lot# |
|---|---|---|---|
| sjTREC | ZEN00403 (Lot 1) | Adult whole blood | W36981900296700 |
|  | ZEN00410 (Lot 2) | Leukocyte Depleted Blood | W36981900281700 |
|  | ZEN00409 (Lot 3) | Leukocyte Depleted Blood | W36981900270500 |
| KREC | ZEN00403 (Lot 1) | Leukocyte Depleted Blood | W36981900270800 |
|  | ZEN00410 (Lot 2) | Leukocyte Depleted Blood | W36981900281700 |
|  | ZEN00409 (Lot 3) | Leukocyte Depleted Blood | W36981900270500 |

Each cord blood sample was diluted into different levels in which at least the lowest three levels shall yield hit rates within the range of 0.10 to 0.90 using the corresponding diluents (Table 6). The samples were then spotted onto Ahlstrom 226 filter paper and dried overnight. Then they were stored at −30° C. to −16° C. in a sealed bag with desiccant until use. The final dilutions used in the study and their corresponding hit rates (10 replicates) observed in a pre-test are summarized in Table 7.

TABLE 7

| Analyte Name | CordBlood Sample | Sample Level | Concentration (copies/μL blood) | Dilution factors | Hit rates |
|---|---|---|---|---|---|
| sjTREC | L1 (ZEN00403) | CordBlood | 368 | 1.00 | 100% |
|  | L1 (ZEN00403) | Level 1 | 184 | 2.00 | 100% |
|  | L1 (ZEN00403) | Level 2 | 110 | 3.33 | 100% |
|  | L1 (ZEN00403) | Level 3 | 73.6 | 5.00 | 100% |
|  | L1 (ZEN00403) | Level 4 | 36.8 | 10.0 | 50% |
|  | L1 (ZEN00403) | Level 5 | 29.4 | 12.5 | 50% |
|  | L1 (ZEN00403) | Level 6 | 22.1 | 16.7 | 10% |
|  | L1 (ZEN00403) | Level 7 | 14.7 | 25.0 | 0% |
|  | L1 (ZEN00403) | Diluent | 0 | N/A | 0% |
|  | L2 (ZEN00410) | CordBlood | 492 | 1.00 | 100% |
|  | L2 (ZEN00410) | Level 1 | 55.2 | 6.67 | 100% |

TABLE 7-continued

| Analyte Name | CordBlood Sample | Sample Level | Concentration (copies/μL blood) | Dilution factors | Hit rates |
|---|---|---|---|---|---|
| | L2 (ZEN00410) | Level 2 | 36.8 | 10.0 | 70% |
| | L2 (ZEN00410) | Level 3 | 29.4 | 12.5 | 100% |
| | L2 (ZEN00410) | Level 4 | 14.7 | 25.0 | 60% |
| | L2 (ZEN00410) | Level 5 | 11.0 | 33.3 | 30% |
| | L2 (ZEN00410) | Level 6 | 7.36 | 50.0 | 30% |
| | L2 (ZEN00410) | Level 7 | 3.68 | 100 | 0% |
| | L2 (ZEN00410) | Diluent | 0 | N/A | 0% |
| | L3 (ZEN00409) | CordBlood | 344 | 1.00 | 100% |
| | L3 (ZEN00409) | Level 1 | 110 | 3.33 | 100% |
| | L3 (ZEN00409) | Level 2 | 55.2 | 6.67 | 100% |
| | L3 (ZEN00409) | Level 3 | 29.4 | 12.5 | 70% |
| | L3 (ZEN00409) | Level 4 | 22.1 | 16.7 | 90% |
| | L3 (ZEN00409) | Level 5 | 14.7 | 25.0 | 40% |
| | L3 (ZEN00409) | Level 6 | 11.0 | 33.3 | 20% |
| | L3 (ZEN00409) | Level 7 | 7.36 | 50.0 | 30% |
| | L3 (ZEN00409) | Level 8 | 3.68 | 100 | 10% |
| | L3 (ZEN00409) | Diluent | 0 | N/A | 0% |
| KREC | L1 (ZEN00403) | CordBlood | 1132 | 1.00 | 100% |
| | L1 (ZEN00403) | Level 1 | 792.4 | 1.43 | 100% |
| | L1 (ZEN00403) | Level 2 | 679.2 | 1.67 | 100% |
| | L1 (ZEN00403) | Level 3 | 566.0 | 2.00 | 100% |
| | L1 (ZEN00403) | Level 4 | 226.4 | 5.00 | 100% |
| | L1 (ZEN00403) | Level 5 | 90.56 | 12.5 | 100% |
| | L1 (ZEN00403) | Level 6 | 33.96 | 33.3 | 50% |
| | L1 (ZEN00403) | Level 7 | 11.32 | 100 | 40% |
| | L1 (ZEN00403) | Diluent | 0 | N/A | 0% |
| | L2 (ZEN00410) | CordBlood | 1174 | 1.00 | 100% |
| | L2 (ZEN00410) | Level 1 | 176.1 | 6.67 | 100% |
| | L2 (ZEN00410) | Level 2 | 117.4 | 10.0 | 100% |
| | L2 (ZEN00410) | Level 3 | 93.92 | 12.5 | 100% |
| | L2 (ZEN00410) | Level 4 | 46.96 | 25.0 | 90% |
| | L2 (ZEN00410) | Level 5 | 35.22 | 33.3 | 80% |
| | L2 (ZEN00410) | Level 6 | 23.48 | 50.0 | 50% |
| | L2 (ZEN00410) | Level 7 | 11.74 | 100 | 60% |
| | L2 (ZEN00410) | Diluent | 0 | N/A | 0% |
| | L3 (ZEN00409) | CordBlood | 910.0 | 1.00 | 100% |
| | L3 (ZEN00409) | Level 1 | 273.0 | 3.33 | 100% |
| | L3 (ZEN00409) | Level 2 | 136.5 | 6.67 | 100% |
| | L3 (ZEN00409) | Level 3 | 72.80 | 12.5 | 100% |
| | L3 (ZEN00409) | Level 4 | 54.60 | 16.7 | 100% |
| | L3 (ZEN00409) | Level 5 | 36.40 | 25.0 | 80% |
| | L3 (ZEN00409) | Level 6 | 27.30 | 33.3 | 50% |
| | L3 (ZEN00409) | Level 7 | 18.20 | 50.0 | 50% |
| | L3 (ZEN00409) | Level 8 | 9.10 | 100 | 30% |
| | L3 (ZEN00409) | Diluent | 0 | N/A | 0% |

The LoB study was performed using two sets of NeoMDx™ assay systems and run in 5 days totalling 10 runs. The DNA extraction and PCR setup were done on JANUS™ automated liquid handlers (Perkin Elmer, Waltham, MA For the TREC/KREC/SMN1 LoB determination, five contrived analyte-negative samples (CANS) were used and 6 replicates were tested in each run, totalling 300 results. For the RPP30 LoB determination, blank samples were used (no template DNA), 20 replicates were tested in each run, totalling 200 results. In every plate, kit controls NTC, C1, C2, and C3, assayed in duplicate, were used for run acceptance.

A summary of the overall procedure for the LoB study is shown in Tables 8 (TREC/KREC/SMN1) and 9 (RPP30).

TABLE 8

| Day/Run | Instrument Set | Kit Lot | Sample Results (6 replicates/sample × number of samples) |
|---|---|---|---|
| 1/1 | 1 | 1 | 6 × 5 = 30 |
| 1/2 | 2 | 2 | 6 × 5 = 30 |
| 2/3 | 2 | 1 | 6 × 5 = 30 |
| 2/4 | 1 | 2 | 6 × 5 = 30 |
| 3/5 | 1 | 1 | 6 × 5 = 30 |
| 3/6 | 2 | 2 | 6 × 5 = 30 |
| 4/7 | 2 | 1 | 6 × 5 = 30 |
| 4/8 | 1 | 2 | 6 × 5 = 30 |
| 5/9 | 1 | 1 | 6 × 5 = 30 |
| 5/10 | 2 | 2 | 6 × 5 = 30 |
| Results/kit lot | | | 150 |
| Results/Instrument set | | | 150 |
| Results/sample | | | 60 |
| Results/sample/kit lot | | | 30 |
| Total number of results | | | 300 |

TABLE 9

| Day/Run | Instrument Set | Kit lot | Replicates |
|---|---|---|---|
| 1/1 | 1 | 1 | 20 |
| 1/2 | 2 | 2 | 20 |

TABLE 9-continued

| Day/Run | Instrument Set | Kit lot | Replicates |
|---|---|---|---|
| 2/3 | 2 | 1 | 20 |
| 2/4 | 1 | 2 | 20 |
| 3/5 | 1 | 1 | 20 |
| 3/6 | 2 | 2 | 20 |
| 4/7 | 2 | 1 | 20 |
| 4/8 | 1 | 2 | 20 |
| 5/9 | 1 | 1 | 20 |
| 5/10 | 2 | 2 | 20 |
| Results/kit lot | | | 100 |
| Results/Instrument set | | | 100 |
| Total number of results | | | 200 |

For the LoD and LoQ studies, for each analyte sjTREC or KREC, DNA extraction and PCR setup were done on JANUS automated liquid handlers. For each sample and each dilution, including negative samples (diluents), five replicates were tested in each run, totalling 960 results with 20 replicates per dilution per lot. Each run consisted of a full 96-well plate plus a partial 96-well plate, consolidated into a 384-well plate. A summary of the overall procedure for LoD and LoQ studies is shown in Table 10.

TABLE 10

| Day/Run | Instrument Set | Kit Lot | Sample Results (5 replicates/sample × number of samples × dilutions per sample) |
|---|---|---|---|
| 1/1 | 1 | 1 | 5 × 3 × 8 = 120 |
| 1/2 | 2 | 2 | 5 × 3 × 8 = 120 |
| 2/3 | 2 | 1 | 5 × 3 × 8 = 120 |
| 2/4 | 1 | 2 | 5 × 3 × 8 = 120 |
| 3/5 | 1 | 1 | 5 × 3 × 8 = 120 |
| 3/6 | 2 | 2 | 5 × 3 × 8 = 120 |
| 4/7 | 2 | 1 | 5 × 3 × 8 = 120 |
| 4/8 | 1 | 2 | 5 × 3 × 8 = 120 |
| Results/kit lot | | | 480 |
| Results/Instrument set | | | 480 |
| Results/dilution/sample/kit lot | | | 20 |
| Results/sample/kit lot | | | 160 |
| Total number of results | | | 960 |

For the LoB study, the percentage of false-positive results of each measurand was calculated for each reagent lot. If the percentage of false-positive results for a given reagent lot does not exceed 5%, LoB=zero is confirmed for that lot and for that measurand. Each reagent lot was confirmed separately.

For TREC, KREC and SMN1, all the replicates had no Ct value reported for either of the three analytes. Therefore, the percentage of false-positive results, defined as the percentage of replicates of the contrived analyte-negative sample that had a valid Ct value reported for the corresponding measurand (excluding the replicates that were reported as "Invalid" due to RPP30>28.4) was zero for both kit lots.

For RPP30, there were only two replicates having Ct values reported at 34.59 and 36.23. Therefore, the percentage of false-positive results, defined as the percentage of replicates of the blank sample that has a valid RPP30 Ct value <28.4, was also zero for both kit lots.

A summary of the measurement results of all the LoB study samples for KREC, SMN1 and TREC is shown in Table 11. There were no false-positive results with any of the analytes and thus false positive rates were 0% with both kit lots.

TABLE 11

| Kit Lot | Analyte | N | False Positive | Negative | False Positive % |
|---|---|---|---|---|---|
| Lot1 | KREC | 150 | 0 | 150 | 0.00 |
| | SMN1 | 150 | 0 | 150 | 0.00 |
| | TREC | 150 | 0 | 150 | 0.00 |
| Lot2 | KREC | 150 | 0 | 150 | 0.00 |
| | SMN1 | 150 | 0 | 150 | 0.00 |
| | TREC | 150 | 0 | 150 | 0.00 |

A summary of the measurement results of all the blank samples for RPP30 is shown in Table 12. There were no false-positive results with RPP30 and thus false positive rates were 0% with both kit lots.

TABLE 12

| Kit Lot | Analyte | N | False Positive | Negative | False Positive % |
|---|---|---|---|---|---|
| Lot1 | RPP30 | 100 | 0 | 100 | 0.00 |
| Lot2 | RPP30 | 100 | 0 | 100 | 0.00 |

For the LoD and LoQ studies, both LoD and LoQ were calculated in two units: copies/µL blood and copies/$10^5$ cells. To calculate LoD and LoQ in the unit of copies/$10^5$ cells, the initial sjTREC and KREC concentrations (copies/$10^5$ cells) in each cord blood sample were calculated based on the ΔCt values between the mean sjTREC Ct value of the cord blood sample and the mean RPP30 Ct value of all the dilutions derived from the same cord blood sample and the ΔCt values between the mean KREC Ct value of the cord blood sample and the mean RPP30 Ct value of all the dilutions derived from the same cord blood sample using the following two formulas:

$$TREC: 2 \times 2^{-(TREC\ Ct - RPP30Ct)} \times 117000$$

$$KREC: 2 \times 2^{-(KREC\ Ct - RPPCt)} \times 254000$$

The sjTREC and KREC concentrations (copies/$10^5$ cells) in their dilutions were then calculated based on their corresponding dilution factors.

LoD and LoQ were evaluated separately for each analyte, sjTREC or KREC. The data collected from all three cord blood samples and their dilutions were pooled together for the calculation. The LoD were calculated using probit analysis at 95% probability for each reagent kit lot. The LoQ was evaluated as the functional sensitivity which represented the measurand concentration associated with a desired within-laboratory precision. Only the dilutions that yielded 100% hit rates were included in the LoQ calculation. For each qualified dilution, the mean and the SD of the concentrations in Ln (copies/$10^5$ cells) were calculated. A power function model (SD vs the mean concentration) was then used to fit the datasets for each reagent kit lot. The LoQ estimate for each reagent kit lot was determined as the predicted lowest concentration that has within-laboratory precision equal to 90% SD of precision requirements (sjTREC, 0.9 Ln (copies/$10^5$ cells), and KREC, 1.49 Ln (copies/$10^5$ cells)).

The higher value of LoD/LoQ obtained separately from two reagent kit lots was accepted as the assay LoD/LoQ. However, if LoQ happened to be smaller than LoD, the LoD was reported as both assay LoD and assay LoQ, as in theory it is impossible to have LoQ smaller than LoD.

For TREC determined in the LoD study, the number of positive results observed, total number of measurements and calculated hit rate percentages are shown in Table 13 along with sample concentrations in both units: copies/µL blood and copies/$10^5$ cells.

TABLE 13

| Kit Lot | Cord Blood Samp. | Sample Level | Conc. in copies/μL blood | Dilut. | Conc. in copies/$10^5$ cells | Obs'd Pos. | Obs'd Neg. | Hit Rate % |
|---|---|---|---|---|---|---|---|---|
| 1 | L1 | CordBlood | 368 | 1.00 | 1436 | 0 | 20 | 100% |
| 1 | L1 | Level 1 | 184 | 2.00 | 718 | 0 | 20 | 100% |
| 1 | L1 | Level 2 | 110 | 3.33 | 431 | 0 | 20 | 100% |
| 1 | L1 | Level 3 | 73.6 | 5.00 | 287 | 0 | 20 | 100% |
| 1 | L1 | Level 4 | 36.8 | 10.0 | 144 | 5 | 15 | 75% |
| 1 | L1 | Level 5 | 29.4 | 12.5 | 115 | 6 | 14 | 70% |
| 1 | L1 | Level 6 | 22.1 | 16.7 | 86 | 9 | 11 | 55% |
| 1 | L1 | Level 7 | 14.7 | 25.0 | 57 | 12 | 8 | 40% |
| 1 | L1 | Diluent | 0 | N/A | 0 | 18 | 2 | 10% |
| 1 | L2 | CordBlood | 492 | 1.00 | 4207 | 0 | 20 | 100% |
| 1 | L2 | Level 1 | 55.2 | 6.67 | 631 | 0 | 20 | 100% |
| 1 | L2 | Level 2 | 36.8 | 10.0 | 421 | 2 | 18 | 90% |
| 1 | L2 | Level 3 | 29.4 | 12.5 | 337 | 2 | 18 | 90% |
| 1 | L2 | Level 4 | 14.7 | 25.0 | 168 | 11 | 9 | 45% |
| 1 | L2 | Level 5 | 11.0 | 33.3 | 126 | 10 | 10 | 50% |
| 1 | L2 | Level 6 | 7.36 | 50.0 | 84 | 13 | 7 | 35% |
| 1 | L2 | Level 7 | 3.68 | 100 | 42 | 17 | 3 | 15% |
| 1 | L2 | Diluent | 0 | N/A | 0 | 20 | 0 | 0% |
| 1 | L3 | CordBlood | 344 | 1.00 | 2232 | 0 | 20 | 100% |
| 1 | L3 | Level 1 | 110 | 3.33 | 669 | 0 | 20 | 100% |
| 1 | L3 | Level 2 | 55.2 | 6.67 | 335 | 2 | 18 | 90% |
| 1 | L3 | Level 3 | 29.4 | 12.5 | 179 | 3 | 17 | 85% |
| 1 | L3 | Level 4 | 22.1 | 16.7 | 134 | 7 | 13 | 65% |
| 1 | L3 | Level 5 | 14.7 | 25.0 | 89 | 5 | 15 | 75% |
| 1 | L3 | Level 6 | 11.0 | 33.3 | 67 | 9 | 11 | 55% |
| 1 | L3 | Level 7 | 7.36 | 50.0 | 45 | 14 | 6 | 30% |
| 1 | L3 | Level 8 | 3.68 | 100 | 22 | 16 | 4 | 20% |
| 1 | L3 | Diluent | 0 | N/A | 0 | 20 | 0 | 0% |
| 2 | L1 | CordBlood | 368 | 1.00 | 1175 | 0 | 20 | 100% |
| 2 | L1 | Level 1 | 184 | 2.00 | 588 | 0 | 20 | 100% |
| 2 | L1 | Level 2 | 110 | 3.33 | 353 | 0 | 20 | 100% |
| 2 | L1 | Level 3 | 73.6 | 5.00 | 235 | 1 | 19 | 95% |
| 2 | L1 | Level 4 | 36.8 | 10.0 | 118 | 7 | 13 | 65% |
| 2 | L1 | Level 5 | 29.4 | 12.5 | 94 | 16 | 4 | 20% |
| 2 | L1 | Level 6 | 22.1 | 16.7 | 71 | 9 | 11 | 55% |
| 2 | L1 | Level 7 | 14.7 | 25.0 | 47 | 17 | 3 | 15% |
| 2 | L1 | Diluent | 0 | N/A | 0 | 19 | 1 | 5% |
| 2 | L2 | CordBlood | 492 | 1.00 | 2796 | 0 | 20 | 100% |
| 2 | L2 | Level 1 | 55.2 | 6.67 | 419 | 0 | 20 | 100% |
| 2 | L2 | Level 2 | 36.8 | 10.0 | 280 | 3 | 17 | 85% |
| 2 | L2 | Level 3 | 29.4 | 12.5 | 224 | 2 | 18 | 90% |
| 2 | L2 | Level 4 | 14.7 | 25.0 | 112 | 8 | 12 | 60% |
| 2 | L2 | Level 5 | 11.0 | 33.3 | 84 | 6 | 14 | 70% |
| 2 | L2 | Level 6 | 7.36 | 50.0 | 56 | 11 | 9 | 45% |
| 2 | L2 | Level 7 | 3.68 | 100 | 28 | 17 | 3 | 15% |
| 2 | L2 | Diluent | 0 | N/A | 0 | 20 | 0 | 0% |
| 2 | L3 | CordBlood | 344 | 1.00 | 1754 | 0 | 20 | 100% |
| 2 | L3 | Level 1 | 110 | 3.33 | 526 | 2 | 18 | 90% |
| 2 | L3 | Level 2 | 55.2 | 6.67 | 263 | 0 | 20 | 100% |
| 2 | L3 | Level 3 | 29.4 | 12.5 | 140 | 1 | 19 | 95% |
| 2 | L3 | Level 4 | 22.1 | 16.7 | 105 | 6 | 14 | 70% |
| 2 | L3 | Level 5 | 14.7 | 25.0 | 70 | 11 | 9 | 45% |
| 2 | L3 | Level 6 | 11.0 | 33.3 | 53 | 13 | 7 | 35% |
| 2 | L3 | Level 7 | 7.36 | 50.0 | 35 | 15 | 5 | 25% |
| 2 | L3 | Level 8 | 3.68 | 100 | 18 | 17 | 3 | 15% |
| 2 | L3 | Diluent | 0 | N/A | 0 | 20 | 0 | 0% |

Probit analysis in copies/µL blood unit was performed and the results for both kit lots with 95% confidence intervals are summarized in Table 14. The LoD estimate from the concentration value probit analysis gave an estimated hit rate of 95%.

TABLE 14

| Kit Lot | LoD Estimate (copies/$10^5$ cells) | 95% Confidence Interval |
|---|---|---|
| 1 | 438 (RPP30 Ct = 24.6) | 341-620 |
| 2 | 342 (RPP30 Ct = 24.1) | 271-467 |

To estimate the clinical significance of LoD concentration level in copies/$10^5$ cells unit, the RPP30 level of newborn sample distributions was adjusted to the same level as in the LoD samples. Table 15 shows TREC LoD newborn distribution lower percentile values in copies/$10^5$ cells with RPP30 values fixed to LoD kit lot average values. Based on the newborn distribution percentile values, kit lot 1. LoD result was at 0.7% percentile of NB S distribution and kit lot 2. LoD result was at 0.8% percentile of NBS distribution.

TABLE 15

| Kit Lot | LoD Sample RPP30 Average Ct Value | 0.5% percentile | 0.6% percentile | 0.7% percentile | 0.8% percentile |
|---|---|---|---|---|---|
| 1 | 24.6 | 372 | 390 | 440 | 470 |
| 2 | 24.1 | 263 | 276 | 311 | 332 |

For KREC determined in the LoD study, the number of positive results observed, total number of measurements and calculated hit rate percentages are shown in Table 16 along with sample concentrations in both units: copies/µL blood unit and copies/$10^5$ cells.

TABLE 16

| Kit Lot | Cord Blood Sample | Sample Level | Conc. in copies/µL blood | Dilut. | Conc. in copies/$10^5$ cells | Obs'd Pos. | Obs'd Neg. | Hit Rate % |
|---|---|---|---|---|---|---|---|---|
| 1 | L1 | CordBlood | 1132 | 1.00 | 5128 | 0 | 20 | 100% |
| 1 | L1 | Level 1 | 792.4 | 1.43 | 3590 | 0 | 20 | 100% |
| 1 | L1 | Level 2 | 679.2 | 1.67 | 3077 | 0 | 20 | 100% |
| 1 | L1 | Level 3 | 566.0 | 2.00 | 2564 | 0 | 20 | 100% |
| 1 | L1 | Level 4 | 226.4 | 5.00 | 1026 | 1 | 19 | 95% |
| 1 | L1 | Level 5 | 90.56 | 12.5 | 410 | 4 | 16 | 80% |
| 1 | L1 | Level 6 | 33.96 | 33.3 | 154 | 7 | 13 | 65% |
| 1 | L1 | Level 7 | 11.32 | 100 | 51 | 17 | 3 | 15% |
| 1 | L1 | Diluent | 0 | N/A | 0 | 20 | 0 | 0% |
| 1 | L2 | CordBlood | 1174 | 1.00 | 10102 | 0 | 20 | 100% |
| 1 | L2 | Level 1 | 176.1 | 6.67 | 1515 | 0 | 20 | 100% |
| 1 | L2 | Level 2 | 117.4 | 10.0 | 1010 | 1 | 19 | 95% |
| 1 | L2 | Level 3 | 93.92 | 12.5 | 808 | 0 | 20 | 100% |
| 1 | L2 | Level 4 | 46.96 | 25.0 | 404 | 6 | 14 | 70% |
| 1 | L2 | Level 5 | 35.22 | 33.3 | 303 | 7 | 13 | 65% |
| 1 | L2 | Level 6 | 23.48 | 50.0 | 202 | 7 | 13 | 65% |
| 1 | L2 | Level 7 | 11.74 | 100 | 101 | 11 | 9 | 45% |
| 1 | L2 | Diluent | 0 | N/A | 0 | 20 | 0 | 0% |
| 1 | L3 | CordBlood | 910.0 | 1.00 | 7438 | 0 | 20 | 100% |
| 1 | L3 | Level 1 | 273.0 | 3.33 | 2231 | 0 | 20 | 100% |
| 1 | L3 | Level 2 | 136.5 | 6.67 | 1116 | 0 | 20 | 100% |
| 1 | L3 | Level 3 | 72.80 | 12.5 | 595 | 2 | 18 | 90% |
| 1 | L3 | Level 4 | 54.60 | 16.7 | 446 | 2 | 18 | 90% |
| 1 | L3 | Level 5 | 36.40 | 25.0 | 298 | 3 | 17 | 85% |
| 1 | L3 | Level 6 | 27.30 | 33.3 | 223 | 5 | 14 | 74% |
| 1 | L3 | Level 7 | 18.20 | 50.0 | 149 | 16 | 4 | 20% |
| 1 | L3 | Level 8 | 9.10 | 100 | 74 | 11 | 9 | 45% |
| 1 | L3 | Diluent | 0 | N/A | 0 | 20 | 0 | 0% |
| 2 | L1 | CordBlood | 1132 | 1.00 | 4065 | 0 | 20 | 100% |
| 2 | L1 | Level 1 | 792.4 | 1.43 | 2846 | 0 | 20 | 100% |
| 2 | L1 | Level 2 | 679.2 | 1.67 | 2439 | 0 | 20 | 100% |
| 2 | L1 | Level 3 | 566.0 | 2.00 | 2033 | 0 | 20 | 100% |
| 2 | L1 | Level 4 | 226.4 | 5.00 | 813 | 0 | 20 | 100% |
| 2 | L1 | Level 5 | 90.56 | 12.5 | 325 | 2 | 18 | 90% |
| 2 | L1 | Level 6 | 33.96 | 33.3 | 122 | 6 | 14 | 70% |
| 2 | L1 | Level 7 | 11.32 | 100 | 41 | 15 | 5 | 25% |
| 2 | L1 | Diluent | 0 | N/A | 0 | 20 | 0 | 0% |
| 2 | L2 | CordBlood | 1174 | 1.00 | 6548 | 0 | 20 | 100% |
| 2 | L2 | Level 1 | 176.1 | 6.67 | 982 | 0 | 20 | 100% |
| 2 | L2 | Level 2 | 117.4 | 10.0 | 655 | 0 | 20 | 100% |
| 2 | L2 | Level 3 | 93.92 | 12.5 | 524 | 0 | 20 | 100% |
| 2 | L2 | Level 4 | 46.96 | 25.0 | 262 | 1 | 19 | 95% |
| 2 | L2 | Level 5 | 35.22 | 33.3 | 196 | 3 | 17 | 85% |
| 2 | L2 | Level 6 | 23.48 | 50.0 | 131 | 7 | 13 | 65% |
| 2 | L2 | Level 7 | 11.74 | 100 | 65 | 10 | 10 | 50% |
| 2 | L2 | Diluent | 0 | N/A | 0 | 20 | 0 | 0% |
| 2 | L3 | CordBlood | 910.0 | 1.00 | 5721 | 0 | 20 | 100% |

TABLE 16-continued

| Kit Lot | Cord Blood Sample | Sample Level | Conc. in copies/μL blood | Dilut. | Conc. in copies/10⁵ cells | Obs'd Pos. | Obs'd Neg. | Hit Rate % |
|---|---|---|---|---|---|---|---|---|
| 2 | L3 | Level 1 | 273.0 | 3.33 | 1716 | 0 | 20 | 100% |
| 2 | L3 | Level 2 | 136.5 | 6.67 | 858 | 0 | 20 | 100% |
| 2 | L3 | Level 3 | 72.80 | 12.5 | 458 | 2 | 18 | 90% |
| 2 | L3 | Level 4 | 54.60 | 16.7 | 343 | 3 | 17 | 85% |
| 2 | L3 | Level 5 | 36.40 | 25.0 | 229 | 3 | 17 | 85% |
| 2 | L3 | Level 6 | 27.30 | 33.3 | 172 | 5 | 15 | 75% |
| 2 | L3 | Level 7 | 18.20 | 50.0 | 114 | 9 | 11 | 55% |
| 2 | L3 | Level 8 | 9.10 | 100 | 57 | 15 | 5 | 25% |
| 2 | L3 | Diluent | 0 | N/A | 0 | 20 | 0 | 0% |

Probit analysis was performed and the results for both kit lots with 95% confidence intervals are summarized in Tables 17 and 18. The LoD estimate is the concentration value for which probit analysis gave an estimated hit rate of 95%.

TABLE 17

| Kit Lot | LoD Estimate (copies/μL blood) | 95% Confidence Interval |
|---|---|---|
| 1 | 119 | 90-176 |
| 2 | 75 | 59-105 |

TABLE 18

| Kit Lot | LoD Estimate (copies/10⁵ cells) | 95% Confidence Interval |
|---|---|---|
| 1 | 839 (RPP30 Ct = 24.6) | 646-1208 |
| 2 | 409 (RPP30 Ct = 24.1) | 323-572 |

To estimate the clinical significance of LoD concentration level in copies/10⁵ cells unit, the RPP30 level of newborn sample distributions was adjusted the same level as in the LoD samples. Table 19 shows KREC newborn distribution lower percentile values in copies/10⁵ cells when RPP30 values have been fixed to LoD kit lot average values.

TABLE 19

| Kit Lot | LoD Sample RPP30 Average Ct Value | 0.3% percentile | 0.4% percentile | 0.5% percentile | 0.6% percentile |
|---|---|---|---|---|---|
| 1 | 24.6 | 491 | 580 | 759 | 910 |
| 2 | 24.1 | 347 | 410 | 536 | 643 |

Based on the newborn distribution percentile values, kit lot 1. LoD result was at 0.6% percentile of NBS distribution, and kit lot 2. LoD was at 0.4% percentile of NBS distribution.

For TREC determined in the LoQ study, the number of TREC samples with 100% hit rate was 8 with kit lot 1 and 7 with kit lot 2. Therefore, a precision profiling approach was difficult to perform, and a more conservative approach was chosen by comparing each individual sample to within lot variation requirements. Table 20 shows TREC sample precision results compared to within lot specifications.

TABLE 20

| Kit Lot | Sample Level | Conc. in copies/μL Blood | Mean copies/cells | Mean Ln copies/cells | SD Ln Copies per Cells | Spec. within Kit Lot |
|---|---|---|---|---|---|---|
| 1 | L1 T Lvl 3 | 73.6 | 201 | 5.30 | 0.56 | 0.89 |
| 1 | L2 TK Lvl 1 | 55.2 | 293 | 5.68 | 0.75 | 0.86 |
| 1 | L1 T Lvl 2 | 110 | 471 | 6.15 | 0.57 | 0.86 |
| 1 | L3 TK Lvl 1 | 110 | 474 | 6.16 | 0.60 | 0.86 |
| 1 | L1 T Lvl 1 | 184 | 630 | 6.45 | 0.50 | 0.86 |
| 1 | CB L1 | 368 | 1200 | 7.09 | 0.44 | 0.86 |
| 1 | CB L3 | 344 | 1590 | 7.37 | 0.67 | 0.86 |
| 1 | CB L2 | 492 | 1970 | 7.58 | 0.41 | 0.86 |
| 2 | L3 TK Lvl 2 | 55.2 | 156 | 5.05 | 0.79 | 0.92 |
| 2 | L2 TK Lvl 1 | 55.2 | 234 | 5.45 | 0.87 | 0.87 |
| 2 | L1 T Lvl 1 | 184 | 310 | 5.74 | 0.75 | 0.86 |
| 2 | L1 T Lvl 2 | 110 | 396 | 5.98 | 0.60 | 0.86 |
| 2 | CB L1 | 368 | 1140 | 7.04 | 0.39 | 0.86 |
| 2 | CB L3 | 344 | 1480 | 7.30 | 0.59 | 0.86 |
| 2 | CB L2 | 492 | 1780 | 7.49 | 0.37 | 0.86 |

All samples fulfilled precision requirements with both kit lots. Therefore, the lot specific LoQ value was equal to the mean value of the lowest sample or the LoD determined in the LoD study, whichever is higher, as when the value is below LoD, the hit rate is expected to be below 95%, and the LoQ value will not fulfill the precision requirement. Tables 21 and 22 show TREC LoQ estimates in units of copies/μL blood and copies/10⁵ cells units, respectively.

TABLE 21

| Kit Lot | LoD (copies/μL blood) | LoQ Estimate (copies/μL blood) | LoD/LoQ (copies/μL blood) |
|---|---|---|---|
| 1 | 68 | 55.2 | 95 |
| 2 | 95 | 55.2 | |

TABLE 22

| Kit Lot | LoD (copies/$10^5$ cells) | LoQ Estimate (copies/$10^5$ cells) | LoQ (copies/$10^5$ cells) |
|---|---|---|---|
| 1 | 438 (RPP30 Ct = 24.6) | 201 | 342 (RPP30 Ct = 24.1) |
| 2 | 342 (RPP30 Ct = 24.1) | 156 | |

For KREC determined in the LoQ study, the number of KREC samples with 100% hit rate was 10 with kit lot 1 and 12 with kit lot 2. The same conservative approach as with TREC was chosen by comparing each individual sample to a within lot variation requirement. Table 23 shows KREC sample precision results compared to the within lot specification. All samples fulfilled the precision requirement with both kit lots. Therefore, the lot specific LoQ value was be equal to the mean value of the lowest sample, or the LoD value determined previously, whichever is higher, as when the value is below the LoD value, the hit rate is expected to be below 95% and the LoQ value will not fulfill the precision requirement.

TABLE 23

| Kit Lot | Sample Level | Conc. in copies/μL blood | Mean copies/cells | Mean Ln copies/cells | SD Ln Copies per Cells | Spec. within Kit Lot |
|---|---|---|---|---|---|---|
| 1 | L2 TK Lvl 3 | 93.92 | 576 | 6.36 | 0.94 | 1.35 |
| 1 | L2 TK Lvl 1 | 176.1 | 1080 | 6.99 | 0.65 | 1.35 |
| 1 | L3 TK Lvl 2 | 136.5 | 1120 | 7.02 | 0.64 | 1.35 |
| 1 | L3 TK Lvl 1 | 273.0 | 2070 | 7.64 | 0.65 | 1.35 |
| 1 | L1 K Lvl 3 | 566.0 | 2460 | 7.81 | 0.39 | 1.35 |
| 1 | L1 K Lvl 1 | 1132.0 | 3580 | 8.18 | 0.62 | 1.35 |
| 1 | L1 K Lvl 2 | 792.4 | 3630 | 8.20 | 0.45 | 1.35 |
| 1 | CB L2 | 1174 | 4720 | 8.46 | 0.40 | 1.35 |
| 1 | CB L1 | 1132 | 4780 | 8.47 | 0.41 | 1.35 |
| 1 | CB L3 | 910.0 | 5300 | 8.58 | 0.45 | 1.35 |
| 2 | L2 TK Lvl 3 | 93.92 | 356 | 5.87 | 0.79 | 1.35 |
| 2 | L2 TK Lvl 2 | 117.4 | 596 | 6.39 | 0.69 | 1.35 |
| 2 | L3 TK Lvl 2 | 136.5 | 757 | 6.63 | 0.70 | 1.35 |
| 2 | L1 K Lvl 4 | 226.4 | 835 | 6.73 | 0.68 | 1.35 |
| 2 | L2 TK Lvl 1 | 176.1 | 1040 | 6.95 | 0.71 | 1.35 |
| 2 | L3 TK Lvl 1 | 273.0 | 1650 | 7.41 | 0.51 | 1.35 |
| 2 | L1 K Lvl 3 | 566.0 | 1960 | 7.58 | 0.50 | 1.35 |
| 2 | L1 K Lvl 1 | 792.4 | 3140 | 8.05 | 0.52 | 1.35 |
| 2 | L1 K Lvl 2 | 679.2 | 3370 | 8.12 | 0.34 | 1.35 |
| 2 | CB L1 | 1132 | 4070 | 8.31 | 0.34 | 1.35 |
| 2 | CB L2 | 1174 | 4180 | 8.34 | 0.36 | 1.35 |
| 2 | CB L3 | 910.0 | 4840 | 8.48 | 0.50 | 1.35 |

Tables 24 and 25 show KREC LoQ estimates in units of copies/μL blood and copies/$10^5$ cells, respectively.

TABLE 24

| Kit Lot | LoD (copies/μL blood) | LoQ Estimate (copies/μL blood) | LoD/LoQ (copies/μL blood) |
|---|---|---|---|
| 1 | 119 | 93.92 | 119 |
| 2 | 75 | 93.92 | |

TABLE 25

| Kit Lot | LoD (copies/$10^5$ cells) | LoQ Estimate (copies/$10^5$ cells) | LoD/LoQ (copies/$10^5$ cells) |
|---|---|---|---|
| 1 | 839 (RPP30 Ct = 24.6) | 576 | 839 (RPP30 Ct = 24.6) or 593 (RPP30 Ct = 24.1) |
| 2 | 409 (RPP30 Ct = 24.1) | 376 | |

Based on the results of the foregoing LoB, LoD, and LoQ studies, the LoB of the NeoMDx™ assay was 0 copies/μL blood and 0 copies/105 cells for all analytes. The TREC LoD/LoQ of the NeoMDx™ assay was 95 copies/μL blood and 342 copies/105 cells (RPP30 Ct=24.1) and the KREC LoD/LoQ of the NeoMDx™ assay was 119 copies/μL blood and 593 copies/105 cells (RPP30 Ct=24.1).

Other Embodiments

A number of embodiments have been described. Nevertheless, it will be understood that various modifications may be made without departing from the spirit and scope of the disclosure. Accordingly, other embodiments are within the scope of the following claims.

What is claimed is:
1. A method for reducing a false positive measurement in a biological sample using a multispectral analysis system, the method comprising:
calibrating the system using a first signal from a first calibration region of a calibration sample, wherein the calibration sample comprises a plurality of calibration regions on a substrate, and wherein the plurality of calibration regions comprises:
the first calibration region corresponding to a first fluorescent entity, wherein the first calibration region comprises a concentration of the first fluorescent entity in the first calibration region that is larger than a non-zero concentration of a second fluorescent entity in the first calibration region, wherein a fraction of the second fluorescent entity in the first calibration region relative to a total amount of the first and second fluorescent entities in the first calibration region is between 0.02 and 0.08, and wherein said concentration of the first fluorescent entity in the first calibration region and said fraction are configured to reduce spectral cross-talk of the fluorescence emission of the first fluorescent entity in the biological sample into a spectral emission channel for the second fluorescent entity in the biological sample;

measuring a fluorescence emission from the biological sample, wherein the fluorescence emission comprises a first measurement from the first fluorescent entity in the biological sample; and reducing the false positive measurement arising from spectral cross-talk from the first fluorescent entity in the biological sample into the spectral emission channel for the second fluorescent entity in the biological sample by correcting the first measurement from the biological sample with the first signal from the first calibration region.

2. The method of claim 1, wherein the first fluorescent entity is Cy5 and the second fluorescent entity is Cy5.5.

3. The method of claim 1, wherein the calibration sample is a calibration plate comprising a plurality of sample wells.

4. The method of claim 1, wherein a fluorescence emission spectrum of the first fluorescent entity at least partially overlaps with a fluorescence emission spectrum of the second fluorescent entity.

5. The method of claim 1, wherein the first and second fluorescent entities are each associated with spectral emission channels in the multispectral analysis system, and wherein the fluorescence emission from the first fluorescent entity is detected by the multispectral analysis system in the spectral emission channel associated with the second fluorescent entity.

6. The method of claim 1, wherein the biological sample comprises a plurality of fluorescent entities that are each fluorescent dyes.

7. The method of claim 1, wherein the first fluorescent entity is an endogenous fluorescent moiety, and wherein the second fluorescent entity is a fluorescent dye.

8. The method of claim 1, wherein the fraction of the second fluorescent entity in the first calibration region of the calibration sample is between 0.03 and 0.07.

9. The method of claim 1, wherein the fraction of the second fluorescent entity in the first calibration region of the calibration sample is between 0.04 and 0.06.

10. The method of claim 1, further comprising using the calibrated multispectral analysis system to identify one or more gene targets in the biological sample.

11. The method of claim 1, wherein the plurality of calibration regions further comprises a second calibration region corresponding to the second fluorescent entity, wherein the second calibration region comprises a concentration of the second fluorescent entity that is larger than a concentration of the first fluorescent entity, and wherein the second calibration region comprises a non-zero concentration of the first fluorescent entity.

12. The method of claim 11, further comprising:
calibrating the system to detect a fluorescence emission from a second fluorescent entity in the biological sample using the second calibration region of the calibration sample,
wherein the concentration of the second fluorescent entity in the second calibration region is configured to reduce spectral cross-talk between spectral emission channels of the first and second fluorescent entities in the biological sample.

13. The method of claim 11, wherein:
said measuring comprises measuring fluorescence emissions from first and second fluorescent entities in the biological sample; and
said reducing comprises using information from the first and second calibration regions of the calibration sample to calibrate the fluorescence emissions from the first and second fluorescent entities, respectively, in the biological sample.

14. The method of claim 1, further comprising, prior to said calibrating:
selecting the calibration sample comprising the first calibration region to reduce cross-talk from an emission channel of the first fluorescent entity in the biological sample into an emission channel of a second fluorescent entity in the biological sample.

15. The method of claim 1, wherein said calibrating comprises:
selecting a spectral band to measure a fluorescence emission from the first fluorescent entity in the first calibration region;
measuring the fluorescent emission from the first calibration region and corresponding to the first fluorescent entity; and
storing the fluorescent emission from the first calibration region to calibrate the system to measure the fluorescence emission from the first fluorescent entity in the biological sample.

16. A method for reducing a false positive measurement in a biological sample using a multispectral analysis system, the method comprising:
calibrating the system using a first signal from a first calibration region of a calibration sample, wherein at least N fluorescent entities comprise a first fluorescent entity and N-1 different fluorescent entities, wherein the calibration sample comprises N calibration regions on a substrate, and wherein the N calibration regions comprises:
the first calibration region corresponding to the first fluorescent entity, wherein the first calibration region comprises a concentration of the first fluorescent entity in the first calibration region that is larger than a non-zero concentration of at least one other fluorescent entity in the first calibration region, wherein a fraction of the at least one other fluorescent entity in the first calibration region relative to a total amount of the first fluorescent entity and the at least one other fluorescent entity in the first calibration region is between 0.02 and 0.08, and wherein said concentration of the first fluorescent entity in the first calibration region and said fraction are configured to reduce spectral cross-talk of the fluorescence emission of the first fluorescent entity in the biological sample into a spectral emission channel for at least one of the N-1 different fluorescent entities in the biological sample; and
N-1 calibration regions, wherein each calibration region of the N-1 calibration regions corresponds to a single fluorescent entity of the N-1 different fluorescent entities and comprises a concentration of the single fluorescent entity that is larger than concentrations of any other fluorescent entities in the each calibration region;

wherein none of the N calibration regions comprises all of the N fluorescent entities; wherein at least one of the N calibration regions comprises multiple members of the N fluorescent entities; and wherein N is 2 or more;

measuring a fluorescence emission from the biological sample, wherein the fluorescence emission comprises a first measurement from the first fluorescent entity in the biological sample; and reducing the false positive measurement arising from spectral cross-talk from the first fluorescent entity in the biological sample into the spectral emission channel for the at least one of the N-1 different fluorescent entities in the biological sample by correcting the first measurement from the biological sample with the first signal from the first calibration region.

17. The method of claim 16, wherein the first fluorescent entity is Cy5 and the at least one of the N-1 different fluorescent entities comprise Cy5.5.

18. The method of claim 16, wherein the calibration sample is a calibration plate comprising a plurality of sample wells.

19. The method of claim 16, wherein a fluorescence emission spectrum of the first fluorescent entity at least partially overlaps with a fluorescence emission spectrum of at least one of the N-1 different fluorescent entities.

20. The method of claim 16, wherein the at least N fluorescent entities are each associated with spectral emission channels in the multispectral analysis system, and wherein the fluorescence emission from the first fluorescent entity is detected by the multispectral analysis system in the spectral emission channel associated with at least one of the N-1 different fluorescent entities.

21. The method of claim 16, wherein the at least N fluorescent entities are each fluorescent dyes.

22. The method of claim 16, wherein the first fluorescent entity is an endogenous fluorescent moiety, and wherein one or more of the N-1 different fluorescent entities are fluorescent dyes.

23. The method of claim 16, wherein the fraction of the at least one other fluorescent entity in the first calibration region of the calibration sample is between 0.03 and 0.07.

24. The method of claim 16, further comprising using the calibrated multispectral analysis system to identify one or more gene targets in the biological sample.

* * * * *